United States Patent [19]

Bhatnagar et al.

[11] Patent Number: 5,776,900
[45] Date of Patent: Jul. 7, 1998

[54] HEMOREGULATORY PEPTIDES

[75] Inventors: Pradip Kumar Bhatnagar, Exton; William Francis Huffman, Malvern, both of Pa.; James Edward Talmadge, Bellevue, Nebr.

[73] Assignee: SmithKline Beecham Corporation, Philadelphia, Pa.

[21] Appl. No.: 453,123

[22] Filed: May 30, 1995

Related U.S. Application Data

[63] Continuation of Ser. No. 1,905, Jan. 8, 1993, Pat. No. 5,620,957, which is a continuation-in-part of Ser. No. 819,024, Jan. 10, 1992, abandoned, which is a continuation-in-part of Ser. No. 547,730, Jul. 2, 1990, abandoned, which is a continuation-in-part of Ser. No. 380,578, Jul. 14, 1989, abandoned.

[51] Int. Cl.$^6$ .......................... A61K 38/00; A61K 38/02; C07K 5/00; C07K 7/00
[52] U.S. Cl. .................. 514/15; 514/16; 514/17; 530/327; 530/328
[58] Field of Search .................. 514/15, 16, 17; 530/327, 328

[56] References Cited

U.S. PATENT DOCUMENTS 4,499,081  2/1985  Laerum ........................ 514/17

FOREIGN PATENT DOCUMENTS 9002753  3/1990  WIPO .............................. C07K 7/06
9002754  3/1990  WIPO .............................. C07K 7/06

*Primary Examiner*—Avis M. Davenport
*Attorney, Agent, or Firm*—Linda E. Hall; Stephen A. Venetianer; Edward T. Lentz

[57] ABSTRACT

The invention provides compounds of the general formula:

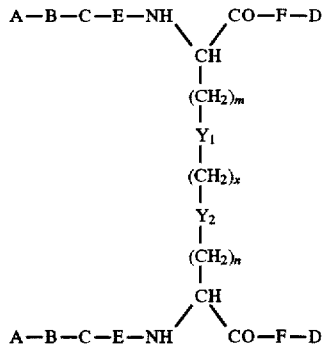

The compounds have hemoregulatory activities and can be used to stimulate haematopoiesis and for the treatment of viral, fungal and bacterial infectious diseases.

10 Claims, No Drawings

HEMOREGULATORY PEPTIDES

This is a continuation of application Ser. No. 08/001,905, filed Jan. 8, 1993 now U.S. Pat. No. 5,620,957 which is a continuation-in-part of Ser. No. 07/819,024 filed Jan. 10, 1992, now abandoned, which is a continuation-in-part of Ser. No. 07/547,730 filed Jul. 2, 1990, now abandoned, which is a continuation-in-part of Ser. No. 07/380,578 filed Jul. 14, 1989, now abandoned.

FIELD OF THE INVENTION

The present invention relates to novel peptides which have hemoregulatory activities and can be used to stimulate haematopoiesis and for the treatment of viral, fungal and bacterial infectious diseases.

BACKGROUND OF THE INVENTION

A variety of regulatory messengers and modifiers such as colony stimulating factors, interferons, and different types of peptides are responsible for the regulation of myelopoiesis. Metcalf, *Cell*, 43:5 (1985); Baserga R., Foa P., Metcalf D, Polli EE (eds), *Biological Regulation of Cell Proliferation* (1986); Nicola et al., *J. Cell Physiol.* 128:501 (1986), Zoumbos et al., *Proyr. Hemat.* 1:341 and 14:201 (1986); Werner et al., *Experientia* 42:521 (1986). Over twenty years ago, Rytomaa and Kivieniemi *Cell Tissue Kinet* 1:329–340 (1968); Rytomaa et al., *Control of Cellular Growth in Adult Organisms* pp 106–138 (1967) reported that extracts of mature granulocytes (granulocytic chalone) could specifically inhibit rat myelopoietic cell proliferation in cover slip cultures. Later, they demonstrated that the factor, which had a molecular weight less than 3,000 daltons, was able to induce the regression of a transplantable rat granulocytic leukemia, as well as retard the growth of leukemia cells in humans. Paukovits and others extracted a similar factor from rat bone marrow cells and showed that it inhibited the titrated thymidine uptake of bone marrow cells, Paukovits, W. R., *Cell Tissue Kinet* 4:539–547 (1971); Naturforsch 37:1297 (1982). In 1979, Boll et al., *Acta Haematologica* 6:130 (1979) demonstrated the inhibitory effects of rat granulocytic extracts on human bone marrow cells in culture and a number of other researchers demonstrated that this crude granulocytic extract inhibited the development of g-CFUC and/or gm-CFUC in vitro from rodent bone marrow cells.

This biological agent was termed a granulocyte chalone which, according to this theoretical concept, should be an endogenous inhibitor of cell proliferation acting in the same tissue as it was secreted. The material obtained from crude extracts was found to be non-species specific but highly tissue specific. Furthermore, it was found to be nontoxic and to have reversible activities.

In 1982, a synthetic hemoregulatory pentapeptide was reported to have a selective inhibitory effect on myelopoietic cells both in vitro and in vivo, where the main effect seems to be on myelopoietic stem cells (CFU-gm), Paukovits et al., Z. Naturforsch 37:1297 (1982) and U.S. Pat. No. 4,499,081. This peptide is believed to be an analogue of a naturally occurring granulopoiesis inhibition factor which has been found in minute quantities in bone marrow extracts.

In 1987, Laerum et al., reported that the oxidation product of this peptide was a dimer (HP-5) formed by disulfide bridges. This dimer has the opposite effect as the monomer as it strongly stimulates colony formation of both human and murine CFU-gm in vitro and up-regulates murine myelopoietic cells in vivo. It is claimed in European Application No. 87309806.5

The dimer is reported as being useful in stimulating myelopoiesis in patients suffering from reduced myelopoietic activity, including bone marrow damage, agranulocytosis and aplastic anemia including patients having depressed bone marrow function due to immunosuppressive treatment to suppress tissue reactions i.e. in bone marrow transplant surgery. It may also be used to promote more rapid regeneration of bone marrow after cytostatic chemotherapy and radiation therapy for neoplastic and viral diseases. It may be of particular value where patients have serious infections due to a lack of immune response following bone marrow failure.

We have now found certain novel synthetic peptides which have a stimulative effect on myelopoietic cells and are useful in the treatment and prevention of viral, fungal and bacterial diseases.

SUMMARY OF THE INVENTION

This invention comprises peptides, hereinafter represented as formula (I), which have hemoregulatory activities and can be used to stimulate haematopoiesis and treat and prevent bacterial, viral and fungal diseases.

These peptides are useful in the restoration of leukocytes in patients with lowered cell counts resulting from a variety of clinical situations, such as surgical induced myelosuppression, AIDS, ARDS, congenital myelodysplacis, bone marrow and organ transplants; in the protection of patients with leukopenia from infection; in the treatment of severely burned patients and in the amelioration of the myelosuppression observed with some cell-cycle specific antiviral agents and in the treatment of infections in patients who have had bone marrow transplants, especially those with graft versus host disease, in the treatment of tuberculosis and in the treatment of fevers of unknown origin in humans and animals. The peptides are also useful in the treatment and prevention of viral, fungal and bacterial infectious diseases, particularly Candida, Herpes and hepatitis in both immunosuppressed and "normal" subjects.

These compounds may also be used in combination with the monomers of co-pending U.S. application Ser. No. 07/799465 and U.S. Pat. No. 4,499,081, incorporated by reference herein, to provide alternating peaks of high and low activity in the bone marrow cells, thus augmenting the natural circadian rhythm of haematopoiesis. In this way, cytostatic therapy can be given at periods of low bone marrow activity, thus reducing the risk of bone marrow damage, while regeneration will be promoted by the succeeding peak of activity. This invention is also a pharmaceutical composition, which comprises a compound of formula (I) and a pharmaceutically acceptable carrier.

This invention further constitutes a method for stimulating the myelopoietic system of an animal, including humans, which comprises administering to an animal in need thereof, an effective amount of a compound of formula (I).

This invention also constitutes a method for preventing and treating viral, fungal and bacterial infections in immunosuppressed and normal animals, including humans, which comprises administering to an animal in need thereof, an effective amount of a compound of formula (I).

DETAILED DESCRIPTION OF THE INVENTION

The peptides of this invention are illustrated by the formula (I):

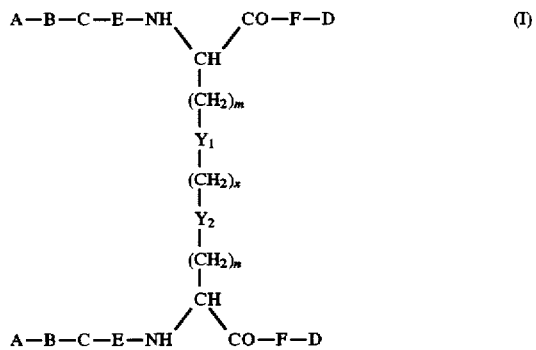

wherein:

$Y_1$ and $Y_2$ are independently $CH_2$ or S;
x is 0, 1, 2, 3, or 4;
m is 0, 1 or 2;
n is 0, 1, or 2;

A is pyroglutamic acid, proline, glutamine, tyrosine, glutamic acid, 2-thiophene carboxylic acid, picolinic acid, cyclohexane carboxylic acid, tetrahydro-2-furoic acid, tetrahydro-3-furoic acid, 2-oxo-4-thiazolidine carboxylic acid, cyclopentane carboxylic acid, 3-thiophene carboxylic acid, (S)-(+)-5-oxo-2-tetrahydrofuran carboxylic acid, pipecolinic acid, pyrrole carboxylic acid, isopyrrole carboxylic acid, pyrazole carboxylic acid, isoimidazole carboxylic acid, triazole carboxylic acid, dithiole carboxylic acid, oxathiole carboxylic acid, isoxazole carboxylic acid, oxazole carboxylic acid, thiazole carboxylic acid, isothiazole carboxylic acid, oxadiazole carboxylic acid, oxatriazole carboxylic acid, oxathiolene carboxylic acid, oxazine carboxylic acid, oxathiazole carboxylic acid, dioxazole carboxylic acid, pyran carboxylic acid, pyrimidine carboxylic acid, pyridine carboxylic acid, pyridazine carboxylic acid, pyrazine carboxylic acid, piperazine carboxylic acid, triazine carboxylic acid, isooxazine carboxylic acid, oxathiazene carboxylic acid, morpholine carboxylic acid, indole carboxylic acid, indolenene carboxylic acid, 2-isobenzazole carboxylic acid, 1,5-pyridine carboxylic acid, pyranol[3,4-b]pyrrole carboxylic acid, isoindazole carboxylic acid, indoxazine carboxylic acid, benzoxazole carboxylic acid, anthranil carboxylic acid, quinoline carboxylic acid, isoquinoline carboxylic acid, cinnoline carboxylic acid, quinazolene carboxylic acid, naphthyridine carboxylic acid, pyrido[3,4-b]-pyridine carboxylic acid, pyrido[3,2-b]-pyridine carboxylic acid, pyrido[4,3-b]pyridine carboxylic acid, 1,3,2-benzoxazine carboxylic acid, 1,4,2-benzoxazine carboxylic acid, 2,3,1-benzoxazine carboxylic acid, 3,1,4-benzoxazine carboxylic acid, 1,2-benzisoxazine carboxylic acid, 1,4-benzisoxazine carboxylic acid, carbazole carboxylic acid, acridine carboxylic acid, or purine carboxylic acid;

B is serine, threonine, glutamic acid, tyrosine or aspartic acid;

C is glutamic acid, tyrosine, aspartic acid, serine, alanine, phenylalanine, histidine, isoleucine, leucine, methionine, tyrosine, threonine, trytophan, norleucine, allothreonine, glutamine, asparagine, valine, proline, glycine, lycine, β-alanine or sarcosine;

D is lysine, arginine, tyrosine, N-methylarginine, aspartic acid, ornithine, serine, alanine, phenylalanine, histidine, isoleucine, leucine, methionine, threonine, trytophan, norleucine, allothreonine, glutamine, asparagine, valine, proline, glycine, lycine, b-alanine, sarcosine, or diaminohexynoic acid; or the carboxyamide, or hydroxy methyl derivative thereof;

E is glutamic acid, aspartic acid, tyrosine or a peptide bond;

F is tyrosine or a peptide bond;

Provided that:

when $Y_1$ and $Y_2$ are S, x is 2, 3 or 4 and m and n are 1; or when $Y_1$ and $Y_2$ are $CH_2$, x is 0, 1 or 2 and m and n are 0; or when $Y_1$ is S and $Y_2$ is $CH_2$, x is 0 and n is 1; or when $Y_2$ is S and $Y_1$ is $CH_2$, x is 0 and m is 1 or;

when C is chosen from the group consisting of serine, alanine, phenylalanine, histidine, isoleucine, leucine, methionine, tyrosine, threonine, trytophan, norleucine, allothreonine, glutamine, asparagine, valine, proline, glycine, β-alanine or sarcosine; D is chosen from the group consisting of: serine, alanine, phenylalanine, histidine, isoleucine, leucine, methionine, tyrosine, threonine, trytophan, norleucine, allothreonine, glutamine, asparagine, valine, proline, glycine, β-alanine or sarcosine; or a pharmaceutically acceptable salt thereof.

Also included in this invention are pharmaceutically acceptable salt complexes of the compounds of this invention. It should be noted in formula (I) that A comprises the terminal amino group. Similarly, D comprises the terminal carboxyl group, or the carboxamide or hydroxy methyl derivative thereof.

The abbreviations and symbols commonly used in the art are used herein to describe the peptides:

Ala=alanine
pGlu=pyroglutamic acid
Pro=proline
Glu=glutamic acid
Asp=aspartic acid
Tyr=tyrosine
Pic=picolinic acid
Ppc=pipecolinic acid
Ppg=propargyl glycine
Gly=glycine
Orn=ornithine
p-(NH$_2$)Phe=para-aminophenylalanine
Hna=2,6-diamino-4-hexynoic acid
Lys=lysine
Gln=glutamine
Arg=arginine
Cys=cysteine
Sub=diaminosuberic acid
Pim=diaminopimelic acid
Ser=Serine
Nle=Norleucine
Adp=diaminoadipic acid
Chc=cyclohexane carboxylic acid
Tfc=tetrahydro-2-furoic acid
Otz=2-oxo-4-thiazolidine
Cpa=cyclopentane
Tpc=3-thiophene carboxylic acid
S-Otf=(S)-(+)-5-oxo-2-tetrahydrofuranecarboxylic acid
R-Otf=(R)-(−)-5-Oxo-2-tetrahydrofuranecarboxylic acid In accordance with conventional representation, the amino terminus is on the left and the carboxy terminus is on the right. All chiral amino acids may be in the D or L absolute configuration. All optical isomers are contemplated.

The amino terminus may be protected by acylation. Examples of such protecting groups are, t-butoxycarbonyl (t-Boc), CH$_3$CO and Ar—CO (Ar=benzyl, or phenyl).

The C-terminus may be carboxy as in the case of the natural amino acid or the carboxamide —C(O)NH$_2$ or hydroxymethyl (—CH$_2$—OH) derivative.

Preferred compounds are those in which:

A is pyroglutamic acid, picolinic acid, proline, tyrosine, or pipecolinic acid;

B is glutamic acid, serine, aspartic acid or tyrosine;

C is aspartic acid, glutamic acid, tyrosine or lysine;

D is lysine, or the carboxyamide derivative thereof, arginine, N-methylarginine, 2,6-diamino-4-hexynoic acid, aspartic acid or ornithine;

E is a bond;

Y$_1$ and Y$_2$ are CH$_2$;

x is 0 or 2;

m and n are 0.

More preferred are compounds wherein:

A is pyroglutamic acid, proline or picolinic acid;

B is glutamic acid, aspartic and or serine;

C is aspartic acid or glutamic acid;

D is lysine or the carboxyamide derivative thereof;

E is a bond;

F is a bond;

Y$_1$ and Y$_2$ are CH$_2$; and x is 0 or 2 and the chiral amino acids are in the L absolute configuration.

Especially preferred are:

(pGlu-Glu-Asp)$_2$Sub(Lys)$_2$ [SEQ ID NO: 1]

(pGlu-Glu-Asp)$_2$Adp(Lys)$_2$ [SEQ ID NO: 2]

(pGlu-Glu-Glu)$_2$Sub(Lys)$_2$ [SEQ ID NO: 3]

(pGlu-Asp-Asp)$_2$Sub(Lys)$_2$ [SEQ ID NO: 4]

(Pic-Glu-Asp)$_2$Sub(Lys)$_2$ [SEQ ID NO: 5]

(L-Ppc-Glu-Asp)$_2$Sub(Lys)$_2$ [SEQ ID NO: 6]

(pGlu-Ser-Asp)$_2$Sub(Lys)$_2$ [SEQ ID NO: 7]

(pGlu-Ser-Asp)$_2$Adp(Lys)$_2$ [SEQ ID NO: 8]

(pGlu-Ser-Asp)$_2$Adp(Lys-NH$_2$)$_2$ [SEQ ID NO: 29]

(Pic-Ser-Asp)$_2$Adp(Lys)$_2$ or [SEQ ID NO: 9]

(Pic-Ser-Asp)$_2$Adp(Lys-NH$_2$)$_2$ [SEQ ID NO: 30]

(pGlu-Glu-Asp)$_2$Adp(Tyr-Lys)$_2$ [SEQ ID NO: 10]

(Pic-Glu-Asp)$_2$Adp(Lys)$_2$ [SEQ ID NO: 11]

(p-Glu-Glu-Asp)$_2$Sub(Lys-NH$_2$)2[SEQ ID NO: 38]

(Pic-Glu-Asp)$_2$Adp(Lys-NH$_2$)$_2$ [SEQ ID NO: 31]

The peptides of the invention are prepared by the solid phase technique of Merrifield, *J. Am. Chem. Soc.*, 85, 2149 (1964), or solution methods known to the art may be successfully employed. The methods of peptide synthesis generally set forth in J. M. Stewart and J. D. Young, "*Solid Phase Peptide Synthesis*", Pierce Chemical Company, Rockford, Ill. (1984) or M. Bodansky, Y. A. Klauser and M. A. Ondetti, "*Peptide Synthesis*", John Wiley & Sons, Inc., New York, NY. (1976) may be used to produce the peptides of this invention and are incorporated herein by reference.

Each amino acid or peptide is suitably protected as known in the peptide art. For example, the α-fluoroenylmethyloxycarbonyl group (Fmoc) or t-butoxycarbonyl (t-Boc) group are preferred for protection of the amino group, especially at the α-position. A suitably substituted carbobenzoxy group may be used for the ε-amino group of lysine and benzyl group for the β and γ carboxy groups of Asp and Glu respectively. Suitable substitution of the carbobenzoxy protecting group is ortho and/or para substitution with chloro, bromo, nitro or methyl, and is used to modify the reactivity of the protective group. Except for the t-Boc group, the protective groups are, most conveniently, those which are not removed by mild acid treatment. These protective groups are removed by such methods as catalytic hydrogenation, sodium in liquid ammonia or HF treatment as known in the art.

If solid phase synthetic methods are used, the peptide is built up sequentially starting from the carboxy terminus and working toward the amino terminus of the peptide. Solid phase synthesis is begun by covalently attaching the C terminus of a protected amino acid to a suitable resin, such as benzhydrylamine resin (BHA), methylbenzhydrylamine resin (MBHA) or chloromethyl resin (CMR), as is generally set forth in U.S. Pat. No. 4,244,946 or phenyl acid amino methyl resin (PAM). A BHA or MBHA support resin is used if the carboxy terminus of the product peptide is to be a carboxamide. ACMR or PAM resin is generally used if the carboxy terminus of the product peptide is to be a carboxy group, although this may also be used to produce a carboxamide or ester.

The protective group on the a-amino group is removed by mild acid treatment (i.e. trifluoroacetic acid). Suitable deprotection, neutralization and coupling cycles known in the art are used to sequentially add amino acids without isolation of the intermediate, until the desired peptide has been formed. The completed peptide may then be deblocked and/or split from the carrying resin in any order.

Treatment of a resin supported peptide with HF or HBr/acetic acid splits the peptide from the resin and produces the carboxy terminal amino acid as a carboxylic acid or carboxamide.

If an ester is desired, the CMR or Pam resin may be treated with an appropriate alcohol, such as methyl, ethyl, propyl, butyl or benzyl alcohol, in the presence of triethylamine to cleave the peptide from the resin and product the ester directly.

Esters of the peptides of this invention may also be prepared by conventional methods from the carboxylic acid precursor. Typically, the carboxylic acid is treated with an alcohol in the presence of an acid catalyst. Alternatively, the carboxylic acid may be converted to an activated acyl intermediate, such as an acid halide, and treated with an alcohol, preferably in the presence of a base.

The preferred method for cleaving a peptide from the support resin is to treat the resin supported peptide with anhydrous HF in the presence of a suitable cation scavenger, such as anisole or dimethoxybenzene. This method simultaneously removes all protecting groups, except a thioalkyl group protecting sulfur, and splits the peptide from the resin. Peptides hydrolyzed in this way from the CMR and Pam resins are carboxylic acids, those split from the BHA resin are obtained as carboxamides.

Modification of the terminal amino group of the peptide is accomplished by alkylation or acylation by methods generally known in the art. These modifications may be carried out upon the amino acid prior to incorporation into the peptide, or upon the peptide after it has been synthesized and the terminal amino group liberated, but before the protecting groups have been removed.

Typically, acylation is carried out upon the free amino group using the acyl halide, anhydride or activated ester, of the corresponding alkyl or aryl acid, in the presence of a tertiary amine. Mono-alkylation is carried out most conveniently by reductive alkylation of the amino group with an appropriate aliphatic aldehyde or ketone in the presence of a mild reducing agent, such a lithium or sodium cyanoborohydride. Dialkylation may be carried out by treating the amino group with an excess of an alkyl halide in the presence of a base.

Solution synthesis of peptides is accomplished using conventional methods used for amide bonds. Typically, a protected t-Boc amino acid which has a free carboxyl group is coupled to a protected amino acid which has a free amino group using a suitable coupling agent, such as N,N'-dicyclohexyl carbodiimide (DCC), optionally in the presence of catalysts such as 1-hydroxybenzotriazole (HOBT) or dimethylamino pyridine (DMAP). Other methods, such as the formation of activated esters, anhydrides or acid halides, of the free carboxyl of a protected t-Boc-amino- acid, and subsequent reaction with the free amine of a protected amino acid, optionally in the presence of a base, are also suitable. For example, a protected Boc-amino acid or peptide is treated in an anhydrous solvent, such as methylene chloride or tetrahydrofuran (THF), in the presence of a base, such as N-methyl morpholine, DMAP (dimethylaminopyridine) or a trialkyl amine, with isobutyl chloroformate to form the "activated anhydride", which is subsequently reacted with the free amine of another protected amino acid or peptide. The peptide formed by these methods may be deprotected selectively, using conventional techniques, at the amino or carboxy terminus and coupled to other peptides or amino acids using similar techniques. After the peptide has been completed, the protecting groups may be removed as hereinbefore described, such as by hydrogenation in the presence of a palladium or platinum catalyst, treatment with sodium in liquid ammonia, hydrofluoric acid or alkali.

If the final peptide, after it has been deprotected, contains a basic group, an acid addition salt may be prepared. Acid addition salts of the peptides are prepared in a standard manner in a suitable solvent from the parent compound and a slight excess of an acid, such as hydrochloric, hydrobromic, sulfuric, phosphoric, acetic, maleic, succinic or methanesulfonic. The acetate salt form is especially useful. If the final peptide contains an acidic group, cationic salts may be prepared. Typically the parent compound is treated with a slight excess of an alkaline reagent, such as a hydroxide, carbonate or alkoxide, containing the appropriate cation. Cations such as $Na^+$, $K^+$, $Ca^{++}$ and $NH^+_4$ are examples of cations present in pharmaceutically acceptable salts. $Na^+$ and $NH^+_4$ are especially preferred.

In general, in order to exert a stimulatory effect, the peptides of the invention may be administered to human patients by injection in the dose range of 0.5 ng to 1 mg preferably 5–500 ng, or orally in the dose range of 50 ng to 5 mg, for example 0.01 mg to 1 mg per 70 kg body weight per day; if administered by infusion or similar techniques, the dose may be in the range 0.005 ng to 1 mg per 70 kg body weight, for example about 0.03 ng over six days. In principle, it is desirable to produce a concentration of the peptide of about $10^{-15}M$ to $10^{-5}M$ in the extracellular fluid of the patient.

According to a still further feature of the present invention there are provided pharmaceutical compositions comprising as active ingredient one or more compound of formula (I) as herein before defined or physiologically compatible salts thereof, in association with a pharmaceutical carrier or excipient. The compositions according to the invention may be presented for example, in a form suitable for oral, nasal, parenteral or rectal administration.

As used herein, the term "pharmaceutical" includes veterinary applications of the invention. These peptides may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline and water. Solid carriers include starch, lactose, calcium sulfate dihydrate, terra alba, magnesium stearate or stearic acid, talc, pectin, acacia, agar or gelatin. The carrier may also include a sustained release material such a glyceryl monostearate or glyceryl distearate, alone or with a wax. The amount of solid carrier varies but, preferably will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. Capsules containing one or several active ingredients may be produced, for example, by mixing the active ingredients with inert carriers, such as lactose or sorbitol, and filling the mixture into gelatin capsules. When a liquid carrier is used, the preparation will be in the form of a syrup, elixir, emulsion or an aqueous or non-aqueots suspension. Such a liquid formulation may be administered directly p.o. or filled into a soft gelatin capsule. Organ specific carrier systems may also be used.

Alternately pharmaceutical compositions of the peptides of this invention, or derivatives thereof, may be formulated as solutions of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration and contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

For rectal administration, a pulverized powder of the peptides of this invention may be combined with excipients such as cocoa butter, glycerin, gelatin or polyethylene glycols and molded into a suppository. The pulverized powders may also be compounded with an oily preparation, gel, cream or emulsion, buffered or unbuffered, and administered through a transdermal patch.

Nasal sprays may be formulated similarly in aqueous solution and packed into spray containers either with an aerosol propellant or provided with means for manual compression.

Dosage units containing the compounds of this invention preferably contain 0.1–100 mg, for example 1–50 mg of the peptide of formula (I) or salt thereof.

According to a still further feature of the present invention there is provided a method of inhibition of myelopoiesis which comprises administering an effective amount of a pharmaceutical composition as hereinbefore defined to a subject.

No unacceptable toxicological effects are expected when compounds of the invention are administered in accordance with the present invention.

The biological activity of the compounds of formula I are demonstrated by the following tests.

Induction of Colony Stimulating Activity by Stromal Cells

The human bone marrow stromal cell line, C6, is grown to confluency in plastic tissue culture dishes in RPMI-1640 medium and 5% FBS. On the day prior to the experiment this medium is changed to DMEM without added serum. To these cultures, the compounds are added for one hour, then washed from the cultures. The medium is replaced with fresh DMEM and the cells are incubated for 24 hours at 37° C., 5% $CO_2$. After 24 hours the C6 cell culture supernatant is collected, sterile filtered, and frozen until it can be assayed for the presence of hematopoietic colony stimulating activity (CSA) as set forth below.

Soft Agar Assay

Bone marrow cells are obtained from Lewis rats. They are adjusted to $10^6$ cells/ml in DMEM without serum. A single layer agar system utilizing the following is used: DMEM enriched with nutrients ($NaHCO_3$, pyruvate, amino acids, vitamins, and HEPES buffer); 0.3% Bacto agar, and 20% Lewis rat serum. To this are added dilutions of C6 cell line supernatant (10–2.5%) from above along with rat bone marrow cells (final concentration=$10^5$cells/ml). The agar plates are incubated at 37° C., 5% $CO_2$ for 7–8 days. Colonies of proliferating bone marrow cells (CFU-C) are counted utilizing a microscope. The number of agar colonies counted is proportional to the amount of CSA present within the C6 bone marrow stromal cell line supernatant.

TABLE 1

| | Hematopoietic Colony Stimulating Activity Using 5% Supernatant |
|---|---|
| Dose ng/ml | Percent of Control (pGlu-Glu-Asp)$_2$-Sub-(Lys)$_2$ [SEQ ID NO: 1] (Example 2) |
| 1000 | 192 |
| 100 | 241 |
| 10 | 207 |
| 1 | 188 |
| 0.1 | 154 |
| 0.01 | 97 |
| 0.001 | — |

Herpes Simplex Mouse Model

Seven days prior to infection, Balb/c mice are injected intraperitoneally once a day with a 0.2 ml volume at doses of 10 and 1 ng/kg of compound. Control mice receive injections of 0.1 ml of a mixture of the dilution buffer, DPBS and 0.5% heat inactivated normal mouse serum.

The mice are infected with a Herpes Simplex virus (strain MS) by injecting $5.0 \times 10^5$/pfu suspended in 0.05 mls of PBS in each rear foot pad. The mice continue to get compound or control injections until moribund (unable to get food or water). Usually paralysis of the hind leg occurs approximately eight days after infection. The paralysis progresses until encephalitis occurs.

Alternatively, the virus is inoculated by means of a vaginal route. A cotton plug containing $5.0 \times 10^5$/pfu of the MS-NAP strain is inserted into the vagina of the mouse.

A Wilcoxin test is used to determine if a significant increase in survival is found in the treated verses contol group.

Candida challenge

*Candida albicans* strain B311a is used. This strain has been mouse passed then frozen at −70° C. B311a is virulent to immunosuppressed mice in the range of 5.0 to $8.0 \times 10^4$ cfu/mouse and for normal mice in the range of 1.0 to $2.0 \times 10^5$ cfu/mouse. A sample from the frozen stock of Candida was grown on Sabouroud dextrose slants and then transferred to 50 ml. shake cultures of Sabouroud broth for 18 hours. The cells were washed three times, then counted by hemocytometer, and viability was confirmed by methylene dye exclusion. Viability counts were performed on the inoculum to confirm the counts.

All mice (Balb/c) infected with Candida were infected i.v. with cells suspended in 0.2 mls. of saline. Some mice are sublethally myelodepressed with 300 rads of irradiation. Beginning 2 hours following irradiation, the animals are injected with compound CSF as a positive control, or excipient, daily. Seven days after irradiation and treatment begins, the mice are challenged with *Candida albicans* by intravenous administration. Note that this reprsents approximately a LD75 for normal mice. In other studies the mice are not immunosuppressed. In these studies the mice are treated starting seven days post infection in the same manner as the irradiated mice. In both models the mice are followed until moribund and the change is survival compared using the Wilcoxin test.

The examples which follow serve to illustrate this invention. The examples are intended to in no way limit the scope of this invention, but are provided to show how to make and use the compounds of this invention.

In the examples, all temperatures are in degrees Centigrade. Amino acid analysis were performed upon a Dionex Autoion 100. Analysis for peptide content is based upon Amino Acid Analysis. FAB mass spectra were performed upon a VG ZAB mass spectrometer using fast atom bombardment. The abbreviations used are as follows:

Arg=arginine
Asp=aspartic acid
t-BOC=tert. butyloxy carbonyl
Bz=benzyl
Cl-Z=p-chloro carbobenzyloxy carbonyl (Z=carbobenzyloxy carbonyl)
DCC=dicylohexyl carbodiimide
DIEA=diisopropylethyl amine
EDC=(N-ethyl-N'-(3-dimethylaminopropyl) carbodiimide
Glu=glutamic acid
p-Glu=pyroglutamic acid
Tyr=tyrosine
Hna=diaminohexynoic acid
HOBT=hydroxybenzotriazole
Lys=lysine
NMP=N-methyl-2-pyrrolidinone
Pro=proline
Gln=glutamine
Cys=cysteine $$\text{Pim} = \begin{array}{c} \text{NH—CH—CO} \\ | \\ (CH_2)_3 \\ | \\ \text{NH—CH—CO} \end{array} \text{(diaminopimelic acid)}$$

$$\text{Sub} = \begin{array}{c} \text{NH—CH—CO} \\ | \\ (CH_2)_4 \\ | \\ \text{NH—CH—CO} \end{array} \text{(diaminosuberic acid)}$$

$$\text{Adp} = \begin{array}{c} \text{NH—CH—CO} \\ | \\ (CH_2)_2 \\ | \\ \text{NH—CH—CO} \end{array}$$

N-MeArg=N-methyl arginine
Prc=bis BOC-S,S'-1,3-propanediylcysteine
Etc=bis BOC-S,S'-1,2-ethanediylcysteine
Buc=bis BOC-S,S'-1,4-butanediylcysteine
Chc=cyclohexane carboxylic acid
Tfc=tetrahydro-2-furic acid
Otz=2-oxo-4-thiazolidine
Cpa=cyclopentane
Tpc=3-thiophene carboxylic acid
S-Otf=(S)-(+)-5-oxo-2-tetrahydrofuranecarboxylic acid
R-Otf=(R)-(−)-5-oxo-2-tetrahydrofuranecarboxylic acid
Ppc=pipecolinic acid
Ser=Serine
Nle=Norleucine

EXAMPLE 1

Preparation of: (p-Glu-Glu-Asp)$_2$-Pim-(Lys) 2 [SEQ ID NO: 12]

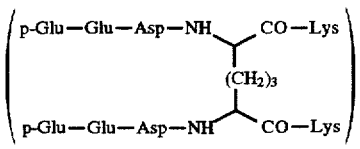

A half gram of t-BOC-Lys(C1-Z)-O CH$_2$-Pam Resin (0.63 mmol/gm) was loaded in the reaction vessel of a Beckman 990 B synthesizer. In the deprotection step, the t-Boc group was removed using 40% trifluoroacetic acid (TFA) in methylene chloride (CH$_2$Cl$_2$) and rinsed with CH$_2$Cl$_2$. The trifluoroacetate salt was neutralized by 10% DIEA/CH$_2$Cl$_2$. Two mM (780 mgs) of Di-BOC-2,6-diaminopimelic acid was coupled using 2 mM of DCC and HOBT. The coupling was done in the mixture of 15 ml of CH$_2$Cl$_2$ and 10 ml of DMF at room temperature for two hours. Kaiser's test was used to monitor the coupling. Any remaining free carboxyl groups were amidated twice by using 3 mM (1.65 gms) of H-Lys(Z)-OBz.HCl and 3 mM of DCC and 3 mM of HOBT in 25 ml of CH$_2$Cl$_2$/DMF (15/10).

After two hours of coupling, the resin was washed twice with 15 ml of CH$_2$Cl$_2$, twice with 15 ml of DMF, twice with 15 ml of MeOH/CH$_2$Cl$_2$ (1:1), and finally twice with 15 ml of CH$_2$Cl$_2$. After the deprotection of t-Boc using 40% TFA/CH$_2$Cl$_2$ and the neutralization using 10% DIEA/CH$_2$Cl$_2$, 2 mM (0.646 gm) of Boc-Asp (Bzl) and 2 mM of DCC and 2 mM of HOBT were added and coupled for 2 hours in 25 ml of CH$_2$Cl$_2$/DMF (15/10). The resin was then subjected to a washing step as described earlier. The deprotection step and the neutralization step were repeated before 2 mM (0.674 gm) of Boc-Glu (Bzl), 2 mM DCC and 2 mM of HOBT were coupled in 25 ml of CH$_2$Cl$_2$/DMF (15/10). After washing, deprotection and neutralization steps, 2mM (0.258 gm) of pGlu, 2 mM of DCC and 2 mM of HOBT were coupled in 25 ml of CH$_2$Cl$_2$/DMF (15/10) for 2 hours before the resin was subjected to a washing step. Completion of the coupling was monitored by Kaiser's test and only single coupling was needed at each step. After the completion of the synthesis the resin was dried and weighed. Yield: 1.2 g.

The peptide resin (1.2 gm) was charged in a cleavage apparatus and cleaved using 10 ml of hydrofluoric acid (HF) and 1 ml anisole at −15° C. for two hours. After removal of HF under vacuum the mixture of resin and peptide was extensively washed with ether and the peptide was extracted in glacial acetic acid (30 ml). Most of the acid was removed from the extracts on a rotavap and the residue was diluted in water and lyophilized. The acetic acid extract had 810 mgs of crude peptide.

The crude peptide (80 mgs), obtained from acetic acid extraction, was further purified using a preparative C-18 column. It was passed through a pre-equilibrated (in 0.1% TFA/H$_2$O) column. The peptide was eluted using a linear gradient of 80% acetonitrile, 20% H$_2$O and 0.1% TFA.

Three isomers co-eluted (8.52 min). These were separated on a C-18 column using a gradient of 30% (0.1% TFA in CH$_3$CN), 70% (0.1% TFA in H$_2$O) to 80% (0.1% TFA in CH$_3$CN), 20% (0.1% TFA in H$_2$O) over 35 minutes at a flow rate of 1.5 ml/min. The following fractions were eluted:

fraction 1: 18.69 min
fraction 2: 19.68 min
fraction 3: 22.95 min

Amino acid analysis gave the following results:

| Amino Acid Analysis | Observed |
|---|---|
| Glu | 1.99 |
| Asp | 1.0 |
| Lys | 1.05 |
| Bis amino pimelic acid | N.D. | mass spec=1157.5 (M+H)$^+$

EXAMPLE 2

Preparation of: (pGlu-Glu-Asp)$_2$-Sub-(Lys)$_2$ [SEQ ID NO: 1]

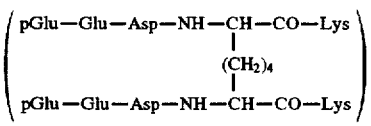

A. Synthesis of BOC-SUB-Lys-($\epsilon$-Z)COOBz.:

Bis-BOC (1.1) diaminosuberic acid (Sub) was synthesized using R. Nutt's method (J. Org. Chem. 45, 3078, 1980).

Two mM of Boc-Sub (808 mg), 4 mM of Lys-($\epsilon$-Z)-COOBz.HCl (1.56 g) and 4 mM of HOBT (0.613 g) were dissolved in 10 ml of methylene chloride (CH$_2$Cl$_2$) and the solution was chilled to −15° C. using an ice/acetone bath. Four mM (0.692 ml) of diisopropyl ethyl amine (DIEA) were added followed by the addition of 0.772 g (4 mM) water soluble carbodiimide (EDC). After stirring for one hour the mixture was allowed to warm to room temperature. After three hours the methylene chloride was evaporated and the residue was dissolved in 200 ml of ethyl acetate. The solution was washed first with 1N HCL, then 1N NaOH, saturated NaCl solution and water. The washes were repeated three times and each wash was about 100 ml. The organic layer was dried over MgSO$_4$ and evaporated. 1.86 g of BOC-Sub-($\epsilon$-Z)Lys-COOBz (79% yield) was obtained and used further without any purification.

B. Synthesis of BOC Asp-($\beta$-OBz)Sub Lys-($\epsilon$-Z)-COOBz.:

BOC-Sub-Lys($\epsilon$-Z)-COOBz (1.8 g) was dissolved in 4N HCl-dioxane for a half hour and then evaporated to dryness. The residue was washed with ether and dried overnight. The hydrochloride salt was dissolved in 30 ml of CH$_2$Cl$_2$ and BOCAsp-($\beta$-OBz) (1.292 g) was added. The solution was chilled to −15° C. and 0.613 g HOBT, 0.554 ml DIEA and 0.772 g of EDC were added. After stirring for two hours the mixture was allowed to warm up to room temperature. After 18 hours (overnight) the reaction mixture was worked up. CH$_2$Cl$_2$ was evaporated and the residue was dissolved in 200 ml of ethyl acetate. The solution was washed with 1N HCl, 1N NaOH, saturated NaCl solution and water (washes were repeated three times and each wash was about 100 ml). The organic layer was dried over MgSO$_4$ and evaporated. BOC-Asp-($\beta$-OBz)-Sub-Lys-($\epsilon$-Z)COOBz 1.9 g (yield 73%). This peptide was used without any further purification.

C. Synthesis of BOC-Glu-($\gamma$-OBz) Asp-($\beta$-OBz) Sub-Lys-($\epsilon$-Z)COOBz.:

BOC-($\beta$-OBz) Asp-Sub-($\epsilon$-Z) Lys-COOBz. 1.8 g was dissolved in 15 ml of 4N HCl dioxane. After fifteen minutes the solvent was removed and the residue was washed with ether and dried. The hydrochloride salt was dissolved in 15 ml of N-methyl pyrrolidone (NMP). The solution is chilled to −15° C. and 4 mM (1.338) of BOC-Glu($\gamma$-OBz), 0.204 ml DIEA, 0.772 g EDC and 0.612 g of HOBT were added. The mixture was stirred over night while gradually warming up to room temperature. The reaction mixture was added to a flask containing one liter of chilled 10% $Na_2CO_3$ in saturated NaCl solution. The precipitates were filtered, washed with water, and dried under vacuum. BOC-(γ-OBz)Glu-(β-OBz)Asp-Sub-(ε-Z)Lys-COOBz (1.3 g) was obtained and used without any further purification. Yield: 68%.

D. Synthesis of pGlu-(γ-OBz) Glu-(β-OBz) Asp-Sub-(ε-Z) Lys-COOBz.:

BOC-(γ-OBz) Glu-(β-OBz)Asp-Sub-(ε-Z)Lys-COOBz 1.2 g was dissolved in 15 ml of 4N HCl dioxane. After fifteen minutes, the solvent was removed and the residue was washed with ether and dried. The hydrochloride salt was dissolved in 15 ml of NMP. The solution is chilled to −15° C. and 4 mM (0.516 g) pyro-Glu(p-Glu), 0.106 ml DIEA, 0.772 g EDC and 0.612 g of HOBT were added. The mixture was stirred overnight while gradually warming up to room temperature. The reaction mixture was added to a flask containing one liter of chilled 10% $Na_2CO_3$ in saturated NaCl solution. The precipitates were filtered, washed with water and dried under vacuum. pGlu-(γ-OBz) Glu-(β-OBz) Asp-Sub-(γ-Z) Lys-COOBz (0.830G) was obtained and used without any further purification. Yield: 69%.

E. Synthesis of pGlu-Glu-Asp-Sub-Lys-COOH: [SEQ ID NO: 32]

pGlu-(γ-OBz) Glu-(β-OBz) Asp-Sub-(ε-Z) Lys-COOBz (0.200 g) was deprotected using 5 ml HF/1.5 ml anisole at 0° C. HF is removed and the peptide is partitioned between ether and 0.1N acetic acid. The aqueous layer is washed and lyophilized. pGlu-Glu-Asp-Sub-Lys-COOH 0.089 g is obtained. Twenty mgs of this peptide are purified on C18 prep VYDAC column using isocratic condition (10% acetonitrile, 90% water and 0.1% trifluoroacetic acid, flow rate 5.6 ml/minute). FAB Mass: M+H=1171.4.Amino Acid Analysis: Asp (1.0), Glu (2.19), Lys (1.01), Sub N.D. HPLC: Retention time on C18 VYDAC 0.23×25 mm analytical column 7.01 minute [flow rate 1.5 ml gradient 0% to 80% B A=0.1% TFA in water and B=0.1% TFA in acetonitrile).

EXAMPLE 3

Preparation of (pGlu-Glu-Asp)$_2$-Lan-(Lys)$_2$ [SEQ ID NO: 13] [Lan=Lanthionine(SCH$_2$CH(NH$_2$)COOH)]

A half gram of t-BOC-Lys(Cl-Z)-CH$_2$ PAM (0.63 m. m/g) is charged in the reaction vessel of a Beckman 990 synthesizer. The t-BOC group is removed using 40% TFA in methylene chloride. The trifluoroacetic acid salt is neutralized by 10% DIEA/CH$_2$Cl$_2$. Two mM of Bis BOC lanthionine is coupled using 4 mM of DCC and HOBT in 15 ml of CH$_2$Cl$_2$ and 10 ml of DMF at room temperature. The Kaiser test is used to monitor the coupling. Any free remaining carboxyl groups are amidated using 3 mM of H-Lys (Z)-OBz.HCl; and 3 mM of DCC and HOBT in 25 ml of CH$_2$Cl$_2$/DMF (15/10). After the coupling resin is extensively washed with CH$_2$Cl$_2$, 30% MeOH-CH$_2$Cl$_2$, and CH$_2$Cl$_2$ (25 ml×3), the cycles of deprotection, neutralization and coupling are repeated with the remaining amino acids in the target peptide (Asp, Glu, pGlu). Four mM of each amino acid, DCC and HOBT are used for each coupling. Each coupling is monitored using Kaiser test. After completion of the synthesis, the resin is dried and weighed.

The peptide resin is charged in cleavage apparatus and cleaved using 10 ml of hydrofluoric acid (HF) and one ml of anisole at −15° C. for two hours. After removal of the HF, the resin is extensively washed with ether and the peptide is extracted with glacial acetic acid (30 ml). Most of the acetic acid is removed on a rotavap and the residue is diluted in water and lyophilized. After purification by HPLC, the peptide is obtained.

EXAMPLE 4

Preparation of (Pro-Asp-Asp)$_2$-Sub-(Lys)$_2$ [SEQ ID NO: 14]

A half gram of t-BOC-Lys(Cl-Z)-CH$_2$ Pam (0.63 m. M/g) is charged in the reaction vessel of a Beckman 990 synthesizer. The t-BOC group is removed using 40% TFA in methylene chloride. The trifluoroacetic acid salt is neutralized by 10% DIEA/CH$_2$Cl$_2$. Two mM of Bis BOC diamino suberic acid is coupled using 4 mM of DCC and HOBT in 15 ml of CH$_2$Cl$_2$ and 10 ml of DMF at room temperature. The Kaiser test is used to monitor the coupling. Any free remaining carboxyl groups are amidated using 3 mM of H-Lys (Z)-OBz.HCl; and 3 mM of DCC and HOBT in 25 ml of CH$_2$Cl$_2$/DMF (15/10). After coupling, the resin is extensively washed with CH$_2$Cl$_2$, 30% MeOH-CH$_2$Cl$_2$, and CH$_2$Cl$_2$, and CH$_2$Cl$_2$ (25 ml×3). The cycles of deprotection, neutralization and coupling are repeated with the remaining amino acids in the target peptide (Asp, Asp, and Pro). Four mM of amino acid, DCC and HOBT are used for each coupling. Each coupling is monitored using the Kaiser test. After completion of the synthesis, the resin was dried and weighed.

The peptide resin is charged in a cleavage apparatus and cleaved using 10 ml of hydrofluoric acid (HF) and one ml of anisole at −15° C. for two hours. After removal of the HF, the resin is extensively washed with ether and the peptide is extracted with glacial acetic acid (30 ml). Most of the acetic acid is removed on a rotavap and the residue is diluted in water and lyophilized. After purification by HPLC, the peptide is obtained.

EXAMPLE 5

Preparation of (pGlu-Asp-Asp)$_2$-Pim-(Lys)$_2$ [SEQ ID NO: 15]

A half gram of BOC-Lys(Cl-Z)-CH$_2$ PAM (0.63 m. M/g) is charged in the reaction vessel of a Beckman 990 synthesizer. The t-BOC group is removed using 40% TFA in methylene chloride. The trifluroacetic acid salt is neutralized by 10% DIEA/CH$_2$Cl$_2$. Two mM of Bis BOC pimelic acid is coupled using 4 mM of DCC and HOBT in 15 ml of CH$_2$Cl$_2$ and 10 ml of DMF at room temperature. The Kaiser test is used to monitor the coupling. Any free remaining carboxyl groups are amidated using 3 mM of H-Lys (Z)-OBz.HCl; and 3 mM of DCC and HOBT in 25 ml of CH$_2$Cl$_2$/DMF (15/10). After coupling, the resin is extensively washed with CH$_2$Cl$_2$, 30% meOH-CH$_2$Cl$_2$, and CH$_2$Cl$_2$ (25 ml×3). The cycles of deprotection, neutralization and coupling are repeated with the remaining amino acids in the target peptide (Asp, Asp, and p-Glu). Four mM of amino acid, DCC and HOBT are used for each coupling. Each coupling is monitored using the Kaiser test. After completion of the synthesis, the resin is dried and weighed.

The peptide resin is charged in a cleavage apparatus and cleaved using 10 ml of hydrofluoric acid (HF) and one ml of anisole at −15° C. for two hours. After removal of the HF, the resin is extensively washed with ether and the peptide is extracted with glacial acetic acid (30 ml). Most of the acetic acid is removed on a rotavap and the residue is diluted in water and lyophilized. Afer purification by HPLC, the peptide is obtained.

EXAMPLE 6

Preparation of (pGlu-Gu-Asp)$_2$-Pim-(Arg-CONH$_2$)$_2$ [SEQ ID NO: 16]

A half gram of BOC-Tos Arg-BHA resin (0.5 m. M/g) is charged in the reaction vessel of a Beckman 990 synthesizer. The BOC group is removed using 40% TFA in methylene chloride. The trifluroacetic acid salt is neutralized by 10% DIEA/CH$_2$Cl$_2$. One mM of Bis BOC pimelic acid is coupled using 2 mM of DCC and HOBT in 15 ml of CH$_2$Cl$_2$ and 10 ml of DMF at room temperature. The Kaiser test is used to monitor the coupling. Any free remaining carboxyl groups are amidated using 3 mM of H-Lys (Z)-OBz.HCl; and 3 mM of DCC and HOBT in 25 ml of CH$_2$Cl$_2$/DMF (15/10). After coupling, the resin is extensively washed with CH$_2$Cl$_2$, 30% MeOH-CH$_2$Cl$_2$, and CH$_2$Cl$_2$ (25 ml×3). The cycles of deprotection, neutralization and coupling are repeated with the remaining amino acids in the target peptide (Asp, Glu and p-Glu). 3 mM of amino acid, DCC and HOBT are used for each coupling. Each coupling is monitored using the Kaiser test. After completion of the synthesis, the resin was dried and weighed.

The peptide resin is charged in a cleavage apparatus and cleaved using 10 ml of hydrofluoric acid (HF) and one ml of anisole at −15° C. for two hours. After removal of the HF, the resin is extensively washed with ether and the peptide is extracted with glacial acetic acid (30 ml). Most of the acetic acid is removed on a rotavap and the residue is diluted in water and lyophilized. After purification by HPLC the peptide is obtained.

EXAMPLE 7

Synthesis of Tyrosine containing analogs:
(Tyr-Glu-Asp)$_2$-Sub-(Lys)$_2$; [SEQ ID NO: 17]
(pGlu-Tyr-Glu-Asp) $_2$-Sub-(Lys)$_2$; [SEQ ID NO: 18]
(pGlu-Glu-Tyr-Asp)$_2$-Sub-(Lys)$_2$; [SEQ ID NO: 19]
(pGlu-Glu-Asp-Tyr) $_2$-Sub-(Lys)$_2$. [SEQ ID NO: 20]

Two grams of BOC-Lys(Cl-Z)-O-Resin (Peninsula Labs®, substitution 0.49 mM/g) was charged in a manual shaker vessel. After deprotection and neutralization steps, 2 mM (808 mg) of di-BOC diaminosuberic acid was coupled to the resin using 4 mM (824 mg) of dicyclohexylcarbodiimide (DCC) and 4 mM (612 mg) of 1-hydroxybenzotriazole hydrate (HOBT) in 25 ml of 50% N-methyl-2-pyrrolidinone (NMP) and dicholoromethane (DCM). The reaction was allowed to proceed overnight followed by the addition of 10 mM (4.06 g) H-Lys (Z)-OBz.HCl. 10 mM (1.29 g) diisopropylethylamine (DIEA), 10 mM (2.06 g) DCC and 10 mM (1.53 g) HOBT. After two hours, the unreacted amino groups were capped using 10% acetic anhydride in NMP/DCM (1:1). Approximately one third of the resulting BOC-Sub-Lys-resin was transferred to another reaction vessel. The major fraction of the resin is called fraction I, and minor fraction is called fraction II. The standard deprotection, neutralization and coupling cycles were used to couple BOC-Tyr (Br-Z), BOC-Asp(OBz), BOC-Glu(OBz), and p-Glu to the resin in fraction II. Five mM of amino acid, DCC and HOBt were used. Coupling was performed in 25 ml NMP/DCM (1/1) and was monitored for completion using the Kaiser test. Five mM of BOC-Asp(OBz) were coupled to the resin in fraction I. One fourth of the resulting BOC-Asp-(OBz)Sub-Lys(Cl-Z) resin was transferred to another vessel (fraction III). The remaining resin is called fraction IV. Standard deprotection, neutralization and coupling cycles were used to couple BOC-Tyr (Br-Z), BOC-Glu(OBz), and p-Glu to resin in fraction III. Five mM of amino acid, DCC and HOBt were used. Coupling was performed in 25 ml NMP/DCM (1/1) and was monitored for completion using Kaiser test. Five mM of BOC-Glu(OBz) were coupled to the resin in the major fraction (fraction IV). One third of this resin was transferred to another vessel and 5 mM of p-Glu were coupled to this fraction (fraction VI) resulting in the synthesis of pGlu-Glu-Asp-Sub-Lys-Resin [SEQ ID NO: 33]. Five mM of BOC Tyr(Br-Z) were coupled to the major fraction (fraction V) and the resin was further split in halves. One half of the resin was saved as is and to the other half of the resin (fraction VII) 5 mM of p-Glu were coupled resulting in the synthesis of p-Glu-Tyr-Glu-Asp-Sub-Lys-Resin [SEQ ID NO: 34]. The scheme is described on the following page:

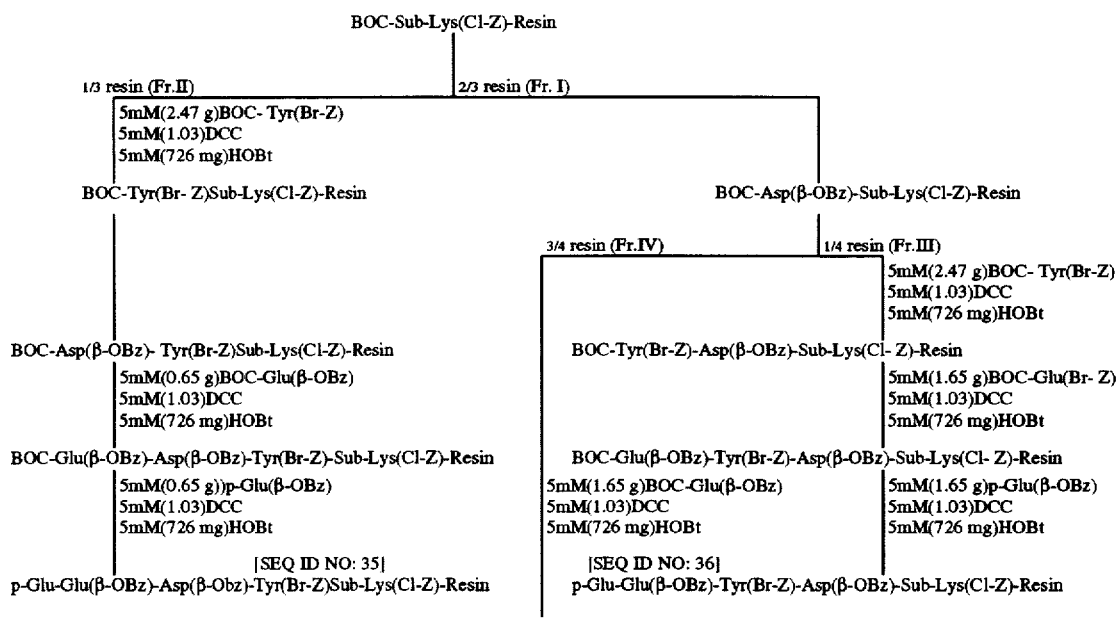

-continued

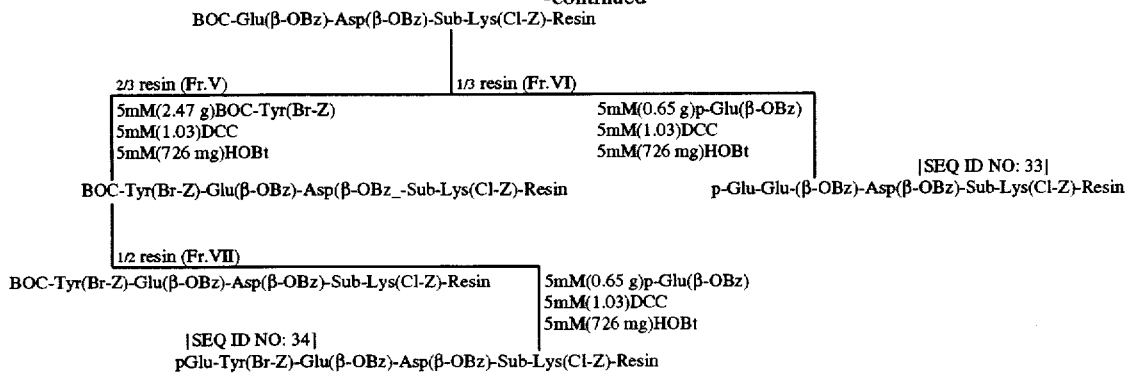

These resin peptides were deprotected and cleaved using HF/anisole at 0° C. for one hour. The crude peptides (approx. 100 mg) were purified on a C-18 VYDAC 2.5 cm×30 cm preparative column using water/0.1% trifluroacetic acid(TFA), and acetonitrile/0.01% TFA buffer system.

| | AMINO ACID ANALYSIS* | | | |
|---|---|---|---|---|
| | FAB/MS (M + H) | Asp | Glu | Sub | Lys |
| (Tyr-Glu-Asp)₂-Sub-(Lys)₂ [SEQ ID NO: 17] | 1274 | 2.08(2) | 2.4(2) | 1.08(1) | 2(2) |
| (pGlu-Tyr-Glu-Asp₂-Sub-(Lys)₂ [SEQ ID NO: 18] | 1497 | 2.1(2) | 3.9(4) | 1.01(1) | 2(2) |
| (pGlu-Glu-Tyr-Asp)₂-Sub-Lys)₂ [SEQ ID NO: 19] | 1497 | 2.2(2) | 3.86(4) | 0.98(1) | 2(2) |
| (pGlu-Glu-Asp-Tyr)₂-Sub-(Lys)₂ [SEQ ID NO: 20] | 1497 | 2.2(2) | 4.06(4) | 1.0(2) | 2(2) |

*The number in the parenthesis indicates the theoretical ratios. The experimental ratios were determined with respect to Lys.

EXAMPLE 8
Preparation of (pGlu Glu Asp)₂Prc(Lys)₂ [SEQ ID NO: 21]
a) Synthesis of Bis BOC-S,S'-1-3-propanediylcysteine:

Three ml of methanol were saturated with dry ammonia and 0.5 g BOC-cysteine in 0.5 ml methanol was added, followed by the addition of 0.35 ml of 1,3 dibromopropane. Ten minutes later, additional 0.5 g of BOC-cysteine in 0.5 ml methanol was added. After 4.5 hrs, the solvent was evaporated and the oily residue dissolved in water. The pH of the solution was adjusted to 9, and the solution was extracted with ether. The aqueous layer was acidified to pH 2 and extracted with ethylacetate. The organic layer was dried and evaporated to yield 1.12 g of Bis BOC-S.S-1,3-propanediylcysteine. The amino acid was used without any further purification. FAB/MS M+H=469.

b) Preparation of (pGluGluAsp)₂Prc(Lys)₂ [SEQ ID NO: 21]

BOC-Lys resin (0.53 g, substitution 0.63 mM/g) was charged in a manual shaker and after deprotection and neutralization cycles, bis BOC-S,S'-1,3-propanediylcysteine (290 mg, 0.6 mM) was coupled using 1 mM (206 mg) DCC and 1 mM (153 mg) HOBt in 10 ml NMP/DCM (1/1). After two hours, the resin was washed with NMP and DCM and 2 mM (765 mg) of H-Lys (Z)-OBz .HCl was added followed by the addition of 1.5 mM (390 mg) DCC and 1.5 mM (230 mg) of HOBt in 4 ml of NMP/DCM (1/1). After 18 hrs, the resin was washed using 20 ml NMP and DCM. Normal deprotection and neutralization and coupling cycles were repeated for the coupling of BOC-Asp(OBz), BOC-Glu (OBz) and p-Glu. One mM of amino acid, DCC and HOBt were used. Coupling was done in 5 ml of NMP/DCM (1/1). Completion of the coupling was monitored using Kaiser's test. The resulting resin peptide (416 mg) was deprotectd and cleaved using 0.5 ml anisole and 8 ml of HF at 0° C. for 2 hrs. HF was evaporated and the peptide resin mixture was washed with ether and extracted with glacial acetic acid. After lyophilization, 130 mg of the crude peptide was obtained. The crude peptide (61.5 mg) was purified on a C 18 VYDAC preparative column using acetonitrile-water (0.1% TFA) buffer system. 16.5 Mg of pure peptide was obtained.

| FAB/MS: M + H 1249.3 | |
|---|---|
| Amino Acid Analysis | |
| Asp | 2.0 (2) |
| Glu | 4.28(4) |
| Dpc | 1.14 |
| Lys | 1.96(2) |

EXAMPLES 9 and 10

Following the procedure for bis BOC-S,S'-1,3-propanediylcysteine (Prc) bis BOC-S,S'-1,2-ethanediylcysteine (Etc) and bis BOC-S,S'-1,4-butanediylcysteine (Buc) were made.

Following the procedures given for (pGluGluAsp)₂PrC (Lys)₂,[SEQ ID NO: 21] 30 mg of (pGluGluAsp)₂Etc-(Lys)₂ [SEQ ID NO: 23] and 17 mg of (pGluGluAsp)₂Buc(Lys)₂ [SEQ ID NO: 22] were made.

EXAMPLE 11
Synthesis of (pGlu-Glu-Asp)₂ Sub(N-MeArg)₂ [SEQ ID NO: 24]

Hydroxy methyl resin 0.5 g (0.45 meq/g) was suspended in DCM (5 ml) and reacted with 0.5 mM (221 mg) BOC-NMe Arg, 0.5 mM (61 mg) dimethylamino pyridine, and 0.5 mM (103 mg) DCC. The acylated resin was washed with DCM (3×), NMP (3×), and DCM (4×). The unreacted hydroxy groups were capped using 0.5 ml phenylisocyanate in 20 ml of DCM. The resin was thoroughly washed with DCM and NMP. The BOC group was removed using 40% TFA/DCM. After neutralization with 10% DIEA in DCM 0.05 mM (20.2 mg), BOC-Sub was coupled using 0.125 mM (25.7 mg) of DCC and 0.125 (19.1 mg) mM HOBt. After 72 hrs, the resin was washed with NMP and DCM. Normal deprotection, neutralization and coupling cycles were repeated for the coupling of BOC-Asp(OBz). BOC-Glu (OBz) and p-Glu. One mM of amino acid, DCC and HOBt were used. Coupling was done in 5 ml of NMP/DCM (1/1). Completion of the coupling was monitored using Kaiser's test. The resulting resin peptide (484 mg) was deprotected and cleaved using 0.5 ml anisole and 10 ml of HF at 0° C. for 2 hrs. The HF was evaporated and the peptide resin mixture was washed with ether and extracted with glacial acetic acid. After lyophilization, 12.5 mg of the crude peptide was obtained. The crude peptide (6 mg) was purified on a C-18 Vydac preparative column using acetonitrile-water (0.1% TFA) buffer system. 2.2 mg of pure peptide was obtained.

EXAMPLE 12

Synthesis of (pGlu-Glu-Asp)$_2$ Sub(Hna)$_2$ [SEQ ID NO: 25]

Hydroxy methyl resin 0.5 g (0.45 meq/g) was suspended in DCM (5 ml) and reacted with 126 mg (0.335 mM) 2,N-BOC-6,N-Z-2,6 diamino-4-hexynoic acid (Hna), 40 mg (0.335) dimethylaminopyridine (DMAP), 69 mg (0.335) DCC and 50 mg (0.335) HOBt. The acylated resin was washed with DCM (3×), NMP (3×), and DCM (4×). Unreacted hydroxy groups were capped using 0.5 ml phenylisocyanate in 20 ml of DCM. The resin was thoroughly washed with DCM and NMP. The BOC group was removed using 40% TFA/DCM. After neutralization with 10% DIEA in DCM. BOC-Sub 44 mg (0.11 mM) was coupled using 50 mg (0.22 mM) of DCC and 33.6 mg (0.11 mM) HOBt. After 16 hrs, the resin was washed using NMP and DCM. Normal deprotection and neutralization and coupling cycles were repeated for the coupling of BOC Asp(OBz), BOC-Glu (OBz) and p-Glu. One mM of amino acid, DCC and HOBt were used. Coupling was done in 5 ml of NMP/DCM (1/1). Completion of the coupling was monitored using Kaiser's test. The resulting resin peptide (608 mg) was deprotectd and cleaved using 0.6 ml anisole and 10 ml of HF at 0° C. for 2 hrs. The HF was evaporated and the peptide resin mixture was washed with ether and extracted with glacial acetic acid. After lyophilization, 93.7 mg of the crude peptide was obtained. The crude peptide (20.6 mg) was purified on a C-18 Vydac preparative column using acetonitrile-water (0.1% TFA) buffer system. 7.5 Mg of pure peptide was obtained. Amino acid analysis and FAB-MS confirmed the structure.

| FAB/MS: M + H 1163 | |
|---|---|
| Amino Acid Analysis | |
| Asp | 2.0 (2) |
| Glu | 4.01(4) |
| Sub | 2.01(1) |
| Hna | 1.44(2) |

EXAMPLE 13

Synthesis of (pGlu-Glu-Asp)$_2$ Adp(Lys)$_2$ [SEQ ID NO: 2]
a) Synthesis of Bis BOC 2,5(S,S)diamino adipic acid.
Bis-BOC 2,5 (s,s) diaminoadipic acid was synthesized using R. Nutt's method (J. Org. Chem. 45, 3078, 1980). To a mixture of 240 ml methanol and 80 ml pyridine, 192 mg NaOCH3 and 57.56 g BOC-Asp (OBz) were added. When the solution was homogeneous, the reaction mixture was cooled to 0° C. Using platinum electrodes, approximately 1.5 amps of current (100 volt) was passed through the reaction mixture. The temperature of the solution was mantained between 15° C. and 25° C. The disappearance of the starting material was followed by TLC (chloroform:methanol:acetic acid/95:4:1) After five hours, the reaction was stopped. The solvent is removed on a rotavap. The oily brown residue was dissolved in 150 ml ethyl acetate. The solution was allowed to stand at room temperature for 18 hours. The precipitates were removed by filtration and the filtrate was evaporated. The crude dibenzyl ester of bis BOC 2,5 diamino adipic acid (61.7 g) was obtained. Sixty one grams of the crude product was loaded on a silica gel column packed in hexane. The column was sequentially eluted with 10%, 20%, 25% and 30% ethyl acetate in hexane. The fractions were analyzed by TLC. Fractions containing the desired product were pooled and solvent was removed on a rotavap. The purified product (3.78 g) was dried in vacuo. Three grams of the dibenzyl ester were dissolved in 120 ml of methanol and hydrogenated in a Parr apparatus using 378 mg of 10% Pd/charcoal. Hydrogenation was completed in five hours. The solution was filtered and the filtrate was concentrated on a rotavap. Crude bis BOC 2,5-diamino adipic acid was purified using flash silica gel chromatography on a column packed in chloroform. The column was sequentially eluted with 98:2:0.1, 98:2:0.5, 95:4:1, 90:8:2, 85:10:5, and 70:20:10 Chloroform, methanol and acetic acid. The fractions containing the desired product were pooled and concentrated on a rotavap and the residue was dried in vacuo (1.07 g). The structure of product was confirmed using NMR, and Mass spectral data.

b) Synthesis of (pGluGluAsp)$_2$Adp(Lys)$_2$ [SEQ NO: 2]

A half gram of BOC-Lys (Cl-Z)-PAM resin (0.63 mM) is charged in a manual shaker vessel. The BOC group is removed using 40% TFA in methylene chloride. The trifluroacetic acid salt is neutralized by 10% DIEA/DCM. 2 mM of Bis BOC 2,5 diamino adipic acid (Adp) is coupled using 4 mM DCC and HOBt in 15 ml DCM and 15 ml NMP. Any free carboxyl groups are amidated using 3 mM H-Lys (Z)-OBz.HCL and 3 mM of DCC and HOBt in 30 ml DCM/NMP (1/1). After coupling, the resin is extensively washed with DCM, NMP. The cycles of deprotection, neutralization and coupling are repeated with the remaining amino acids in the target peptide (Asp,Glu and pGlu). Four mM of each amino acid, DCC and HOBt are used for each coupling. Each coupling is monitored for completion using the Kaiser test. After completion of the synthesis, the resin peptide is charged in cleavage apparatus and cleaved using 10 ml HF and 1 ml anisole at −15° C. for two hrs. After removal of HF the resin is extensively washed with ether and the peptide is extracted in glacial acetic acid. Most of the acetic acid is removed on a rotavap and the residue is diluted with water and lyophilized. After purification by HPLC, the desired peptide is obtained.

EXAMPLES 14–17

| | |
|---|---|
| ((d)-pGlu-Glu-Asp)$_2$-Sub-(Lys)$_2$ | |
| (pGlu-Glu-Glu)$_2$-Sub-(Lys)$_2$ | [SEQ ID NO: 3] |
| (pGlu-(d)-Glu-Asp)$_2$-Sub-(Lys)$_2$ | [SEQ ID NO: 27] |
| (pGlu-Asp-Asp)$_2$-Sub-(Lys)$_2$ | [SEQ ID NO: 4] |

A half gram (0.5 g) of t-BOC-Lys (Cl-Z)-O CH$_2$-Pam Resin (0.63 m mol/gm) was loaded in a manual shaker vessel. In the deprotection step, the BOC group was removed using 40% Trifluoroacetic acid (TFA) in melthylene chloride (CH$_2$Cl$_2$). Trifluoroacetate salt was neutralized by 10% DIEA /CH$_2$Cl$_2$. After the deprotection and neutralization steps, Di-BOC-2,6-diaminosuberic acid (0.16 mM, 66.2 mgs) was coupled using 0.315 mM of DCC and HOBT. The coupling was done in the mixture of 5 ml of CH$_2$Cl$_2$ and 5 ml of DMF at room temperature for four days. Kaiser's test was used to monitor the coupling. The unreacted amino groups were capped using a 10% acetic anhydride/DMF solution. Standard deprotection, neutralization and coupling cycles were then followed and the targeted sequence was assembled. Three mM of amino acid, DCC and HOBt were used. Coupling time was four hours. Completion of the coupling was monitored by Kaiser's test and only single coupling was needed at each step. The peptide resin was loaded in a cleavage apparatus and cleaved using 10 ml of hydrofluoric acid (HF) and 1 ml anisole at −15° C. for two hours. After removal of HF under vacuum, the mixture of resin and peptide was extensively washed with ether and the peptides were extracted in 0.1% TFA and lyophilized. Purification and characterization: The crude peptides were purified using preparative C-18 columns. The column was pre-equilibrated in 99.9% water and 0.1% TFA and the peptide was eluted using a linear gradient of 80% acetonitrile, 20% water and 0.1% TFA. The peptides were analyzed for amino acid composition. The molecular weight was determined using FAB MS. FAB and amino acid analysis for Examples 14–17:

EXAMPLE 14:

FAB MS (M+H 1171.5)

Amino acid analysis: Asp 1.98(2), Glu 4.6(4) and Lys 2(2)

HPLC purity >95%

EXAMPLE 15:

FAB MS(M+H 1199.4)

Amino acid analysis: Glu 5.6(6) and Lys 2(2)

HPLC purity >95%

EXAMPLE 16:

FAB MS (M+H 1171.5)

Amino acid analysis: Asp 1.99(2), Glu 4.6(4) and Lys 2(2)

HPLC purity >95%

EXAMPLE 17:

FAB MS (M+H 1143.5)

Amino acid analysis: Asp 3.99(4), Glu 2.4(2) and Lys 2(2)

HPLC purity >95%

EXAMPLE 18

(Pic-Glu-Asp)$_2$-Sub-(Lys)$_2$ [SEQ ID NO: 5]

a. Synthesis of Boc-Lys(Cl-Z)-Resin

Boc-Lys(Cl-Z) [16.6 g, 40 mmol] was dissolved in 150 ml of 10% H$_2$O in MeOH. The solution was neutralized using 40 ml of 1M CsCO$_3$ solution. The neutralized solution was concentrated using a rotary evaporator. The resulting cesium salt was diluted with DMF and the DMF was removed using a rotary evaporator. This step was repeated two more times. The salt was dried in vacuo for four hours.

The cesium salt of Boc-Lys(Cl-Z) was diluted with 120 ml DMF. To this, was added 20 g of chloromethyl resin (1 meq/g). The reaction mixture was swirled at 40° C. for 48 hours.

The resin was cooled to room temperature and filtered through a fritted funnel and washed sequentially as followed: 500 ml DMF; 500 ml DMF: H$_2$O (1:1); 500 ml DMF; 500 ml MeOH and 1000 ml CH$_2$Cl$_2$. The resin was dried in vacuum. The desired Boc-Lys(Cl-Z)-resin 23.9 g was recovered.

The resin was submitted for amino acid analysis. Based on nitrogen (N) and chlorine (Cl) results, it was calculated that the substitution on the resin was 0.493 meq/g.

b. Synthesis of Boc-Sub-[Lys(Cl-Z)]$_2$-resin

Twenty-three grams (11.339 mmol) of the Boc-Lys(Cl-Z)-resin was transferred into a reaction vessel and was suspended in CH$_2$Cl$_2$.

The Boc protection of the Boc-Lys(Cl-Z) resin was removed by washing the resin with 40 ml 50% TFA in CH$_2$Cl$_2$ for 5 minutes followed by another 40 ml of 50% TFA wash for 30 minutes. The resin was then washed three (3) times with 40 ml CH$_2$Cl$_2$.

The resulting TFA salt was treated twice with 40 ml 10% DIEA in CH$_2$Cl$_2$ for 1 minute, washed once with 40 ml CH$_2$Cl$_2$ and once more with 40 ml of 10% DIEA in CH$_2$Cl$_2$. The resin was thoroughly washed with CH$_2$Cl$_2$ (6×40 ml).

For coupling N,N' di-Boc diaminosuberic acid (Boc-Sub-OH) to the NH2-Lys(Cl-Z)-resin, the resin was suspended in 100 ml methylene chloride (CH$_2$Cl$_2$) in a manual shaker vessel. In another 50 ml flask, 2.29 g (5.66) of Boc-Sub-OH and HOBt (1.53 g, 11.34 mmol) were dissolved in 5 ml N-methyl pyrrolidone (NMP) and 20 ml CH$_2$Cl$_2$. The solution was cooled to 0° C. using an ice bath. To this solution was added DCC (2.34 g, 11.34 mmol) and the reaction mixture was stirred at 0° C. for 15 minutes. The resulting precipitates of dicyclihexylurea were filtered off and the pre-formed active ester was added to the NH$_2$-Lys(2-Cl-Z)-resin suspension. The reaction was monitored using the Kaiser test (Ninhydrin). After 96 hours, the dipeptide-resin was washed with CH$_2$Cl$_2$ (3×40 ml), (3×40 ml) and CH$_2$Cl$_2$ (6×40 ml). Ninhydrin test after work-up gave a slight blue tint solution compared to the negative control. The resin was then washed once with 10% acetic anhydride in CH$_2$Cl$_2$ for 10 minutes and finally with CH$_2$Cl$_2$ (6×40 ml).

c. Synthesis of [Boc-Asp(OBz)]$_2$-Sub-[Lys(Cl-Z)]$_2$-resin:

The TFA deprotection and neutralization steps were repeated to prepare the dipeptide-resin for the Boc-Asp(OBz) coupling. For coupling this amino acid, 3.67 g (11.339 mmol) of Boc-Asp(OBz), 2.34 g (11.339 g) and 1.53 g of HOBt were used. The coupling was complete after 24 hours as indicated by negative ninhydrin test. This tripeptide-resin was also used to make other peptides with different amino acids at position 2 (B).

d. Synthesis of [Boc-Glu(OBz)-Asp(OBz]$_2$-Sub[Lys(Cl-Z)]$_2$-resin

5 Grams (2.465 mmol) of the tripeptide-resin was taken out and was transferred into a smaller reaction vessel. The TFA deprotection and DIEA neutralization steps, as described above, were repeated. For coupling, Boc-Glu (OBzl) [3.66 g, 10.846 mmol], HOBt [1.47 g, 10.846 mmol] and DCC [2.23 g, 10.846 mmol] were used. After 24 hours of coupling, the reaction was complete and [Boc-Glu(OBzl)-Asp(OBzl)]$_2$-Sub-[Lys(Cl-Z]$_2$-resin 5.4 g was recovered. The coupling was done in 60 ml DMF/CH$_2$Cl$_2$. This tetrapeptide was used to make peptides with different amino acids in position 1(A) of compounds of this invention.

e. Synthesis of (Pic-Glu-Asp)$_2$-Sub-(Lys)$_2$ [SEQ ID NO: 5]

The Boc group was removed from the [Boc-Glu(OBzl)]$_2$-Sub-[Lys(Cl-Z)]$_2$-resin (0.5 gm) and 132.8 mg of Picolinic acid (Pic=Pyridine-2-carboxylic acid) was coupled using 146 mg (1.0846 mmol) HOBt and 223 mg (1.0846 mmol) DCC in DMF.

The peptide was deprotected and cleaved from the resin using liquid HF/anisole (10 ml HF and 0.35 ml anisole) at 0° C. for one hour. The HF was removed under vacuum and the peptide/resin mixture was washed with ether and extraced with 0.1% TFA/water solution. The solution was lyophilized. The cleavage of 350 mg of the peptide-resin yielded 110 mg of crude peptide. The crude peptide (50 mg) was purified on a C-18 VYDAC preparative column, using acetonitrile/water TFA buffer system. Eight milligrams of pure peptide were obtained.
FAB MS: (M+H 1159.3)
Amino acid analysis: Asp 1.9(2), Glu 2.2(2) and Lys(2) (Pic and Sub were not analyzed)
HPLC purity >95%

EXAMPLE 19

(pGlu-Ser-Asp)$_2$-Sub-(Lys)$_2$: [SEQ ID NO: 7]

The synthesis of [Boc-Asp(OBzl)]$_2$-Sub-[Lys(Cl-Z)]$_2$-resin is described in Example 18. The Boc group from the [Boc-Asp(OBzl)]$_2$-Sub-[Lys(Cl-Z)]$_2$-resin (0.5 gm) was cleaved and Boc-Ser(OBz)-OH 318.96 mg (1.08 mM) and pGlu 139.45 mg (1.08 mM) were coupled using 146 mg (1.0846 mol) HOBt and 223 mg (1.0846 mmol) DCC in DMF/CH$_2$Cl$_2$. The peptide was deprotected and cleaved from the resin using liquid HF/anisole (10 ml HF and 0.35 ml anisole) at 0° C. for one hour. The HF was removed under vacuum and the peptide/resin mixture was washed with ether and extracted with 0.1% TFA/water solution. The solution was lyophilized. The cleavage of 350 mg of the peptide-resin yielded 125 mg of crude peptide. The crude peptide (50 mg) was purified on a C-18 Vydac preparative column, using acetonitrile/water TFA buffer system. Eleven milligrams of pure peptide were obtained.
FAB MS (M+H 1087.4)
Amino acid analysis: Asp 2.01(2), Ser 1.50(2), Glu 2.6(2) and Lys2(2) (Sub was not analyzed and the value for Ser was not corrected for decomposition during hydrolysis)
HPLC purity >95%

EXAMPLE 20

(Pic-Ser-Asp)$_2$-Adp-(Lys)$_2$: [SEQ ID NO: 9]

The synthesis of Boc-Lys (Cl-Z)-resin, used in the synthsis of this peptide, is described in example 18(a). A similar protocol was used for the synthesis (Boc-Asp(OBz))$_2$-Adp-[Lys(Cl-Z)]$_2$-resin as described in example 18(b) and 18(c) with the exception that N,N' di-Boc diaminosuberic acid (Boc-Sub-OH) was replaced with N,N' di-Boc diaminoadipic acid (Boc-Adp-OH). A half gram of [Boc-Asp(OBz)]$_2$-Adp-[Lys(Cl-Z)]$_2$-resin was used for the synthesis of (Pic-Ser-Asp)$_2$-Adp-(Lys)$_2$ [SEQ ID NO: 9]. The deprotection, neutralization and coupling cycles were repeated with Boc-Ser(Bz)-OH and Picolinic acid. 1.8 mM of amino acids, DCC and HOBt were used in coupling. The couplings were done in 10 ml DMF/CH$_2$Cl$_2$. The peptide-resin 400 mg was cleaved and 113 mg crude peptide were obtained. The crude peptide (50 mg) was purified on a C-18 Vydac preparative column, using acetonitrile/water TFA buffer system. Thirteen milligrams of pure peptide were obtained.
FAB MS (M+H 1047.4)
Amino acid analysis: Asp 2.00(2), Ser 1.62(2), Lys 1.81(2) (Pic and Adp were not analyzed).
HPLC purity >95%

EXAMPLE 21

(Pic-Ser-Asp)$_2$-Adp-(Lys-CONH$_2$)$_2$: [SEQ ID NO: 30]

Five grams of Boc-Lys(Cl-Z)-BHA resin (2.15 mM, substitution=0.43 meq/g, Applied Biosystem Inc.) was charged in shaker vessel and was subjected to standard deprotection and neutralization cycles. N,N' di Boc-diaminoadipic acid (Boc-Adp-OH/404 mg 1.075 mM) was coupled using DCC 974 mg (4.3 mM) and HOBt 638 mg (4.3 mM). The coupling was done in N-methyl pyrrolidone (NMP) and methylene chloride. After seventy-two hours the unreacted amino groups were capped with 10% acetic anhydride in CH$_2$Cl$_2$. After deprotection and neutralization cycles, Boc-Asp(OBz)-OH 3.1 g (9.46 mM) was coupled to the resin using DCC 1.95 g (9.46 mM), HOBt 1.28 g (9.46 mM) in DMF/CH$_2$Cl$_2$. After next deprotection and neutralization cycles the resin was washed with methylene chloride and dried. Half gram of this tripeptide resin was charged in a smaller manual shaker vessel and two other residues (Boc-Ser(OBz)-OH and Pic) were coupled to the resin following the methods described in example 18. The peptide resin (350 mg) was cleaved using HF 10 ml and anisole 0.35 ml. The peptide/resin mixture was washed with ether and the peptide extracted in 0.1% TFA/water solution. The solution was lyophilized to give about 120 mg of crude peptide. Fifty milligrams of crude peptide were purified on a preparative C-18 Vydac column using TFA/acetonitrile/water buffer gradient.
ES MS (M+H 1045.4)
Amino acid analysis: Asp 2.00(2), Ser 1.67(2), Lys 1.74(2).
HPLC purity >95%

EXAMPLE 22

(pGlu-Glu-Asp)$_2$-Adp-(Tyr-Lys)$_2$: (SEQ ID NO: 10]

One gram (0.64 mM) of Boc-Lys(Cl-Z)-resin was charged in a manual shaker vessel. Following the deprotection and neutralization cycles, the resin was coupled to Boc-Tyr(Br-Z)-OH 4.9 g (10 mM) using DCC 2.01 g (10 mM) and HOBt 1.53 g (10 mM). The coupling was done in DMF/CH$_2$Cl$_2$. The completion of the coupling was monitored using Kaiser's test. The Boc group was removed and after neutralization, N,N' Di-Boc-diaminoadipic acid 127.4 mg (0.33 mM) was coupled using DCC 128.4 mg (0.64 mM) and HOBt 98 mg (0.64 mM) in 20 ml DMF/CH$_2$Cl$_2$. The coupling was monitored using Kaiser's test. After 72 hours (the reaction was still not complete) another millimole of DCC (201 mg) and HOBt (153 mg) were added. After another seventy-two hours, the unreacted amino groups were capped with 10% acetic anhydride in methylene chloride. Remaining amino acids were coupled using standard deprotection, neutralization and coupling cycles. Ten millimoles of each amino acid, DCC and HOBt were used. The couplings were done in DMF/CH$_2$C$_{12}$. The entire peptide resin was cleaved using HF 30 ml and anisole 1 ml. The peptide/resin mixture was washed with ether and the peptide was extracted in 0.1% TFA/water. The solution was lyophilized. Three hundred and fifty milligrams of crude peptide were purified on a preparative C-18 column using TFA/acetonitrile/water buffer gradient system. One hundred and twelve milligrams of pure peptide were obtained.
ES MS (M+H 1470.8)
Amino acid analysis: Asp 2.27(2), Glu 4.17(4), Tyr 1.74(2), and Lys 2.(2) (Adp was not analyzed and the value for Tyr was not corrected for decomposition during hydrolysis)
HPLC purity >95%

EXAMPLE 23

(pGlu-Glu-Lys)$_2$-Sub-(Asp)$_2$: |SEQ ID NO: 28|

One gram of Boc-Asp(OcHex*) PAM resin (Bachem CA. 0.5 mM/g) was charged in a manual shaker vessel. Following deprotection and neutralization cycles N,N' di-Boc-diaminosuberic acid was coupled to the resin using the protocol described in Example 18. The standard deprotection, neutralization and coupling protocols were used to couple remaining three amino acids (Boc-Lys(Cl-Z)-OH, Boc-Glu(OBz)-OH and pGlu).

* cyclohexyl

Three millimoles of amino acids, DCC and HOBt were used. The coupling were done in DMF/CH$_2$Cl$_2$. The peptide resin was cleaved using HF 10 ml and anisole 1.0 ml. The peptide/resin mixture was washed with ether and the peptide was extracted in 0.1% TFA/water solution. The solution was lyophilized to give about 4789 mg of crude peptide. Sixty milligrams of crude peptide were purified on a preparative C-18 Vydac column using TFA/acetonitrile/water buffer gradient. Nineteen milligrams of purified peptide were obtained.
ES MS (M+H 1171.4)
Amino acid analysis: Asp 1.98(2), Glu 4.56(2) and Lys 2(2) (Sub was not analyzed)
HPLC purity >95%

EXAMPLES 24–26

By the methods given above the following compounds were made:

(Pic-Glu-Asp)$_2$Adp(Lys)$_2$ [SEQ ID NO: 11]
(pGlu-Glu-Asp)$_2$Sub(Lys-NH$_2$)$_2$ [SEQ ID NO: 40]
(Pic-Glu-Asp)$_2$Adp(Lys-NH$_2$)$_2$ [SEQ ID NO: 31]

EXAMPLE 27

(Pic-Ser-Ala)2-Sub-(Nle-NH$_2$)$_2$ [SEQ ID NO: 39]

Boc-Nle.DCHA (1.24 g, 3.0 mM), HOBt (0.46 g, 3.0 mM) and PyBOP (1.56 g, 3.0 mM) were dissolved together in 10 ml of DMF. DIEA (0.77 ml, 4.5 mM) was added and the mixture was stirred for 10 min. The activated amino acid was then charged in a manual shaker containing 1.61 g (1.0 mM) of p-methylbenzhydrylamine resin swollen in 5 ml of DMF. The resin had previously been treated with 5% DIEA in DMF (2×) and washed with DMF (3×). The reaction vessel was shaken for one hour and 30 minutes at which point the Kaiser's test gave a negative result. The resin was washed with DMF (2×), iPrOH/DCM (1/1) (2×) and DCM (2×), and the Boc group was removed with 33% TFA in DCM. After neutralization with 5% DIEA in DMF, 0.25 mM (101.0 mg) of Boc-Sub was coupled to 0.5 mM of the Nle-resin using 0.5 mM (76.6 mg) of HOBt and 0.5 mM (78.6 µl) DICC in DMF/DCM (¼). After 48 hours the Kaiser's test was slightly positive and additional HOBt and DICC (0.25 mM each) were added to the resin. After 72 hours a quantitative Kaiser's test gave a coupling yield of 93%. The unreacted amino groups were capped using 20% acetic anhydride and 5% DIEA in DMF. Normal deprotection, neutralization and coupling cycles were repeated for the coupling of Boc-Ala, Boc-Ser(OBz) and Pic. 1.5 mM of amino acid, PyBOP and HOBt in 10 ml of DMF were used, and the amino acid was preactivated for 10 minutes after addition of 2.25 mM DIEA before the mixture was added to the resin. Completion of the coupling was monitored using Kaiser's test, and the coupling step was repeated in case of a positive test result. 0.5 g of the resulting resin peptide (1.34 g total obtained) was deprotected and cleaved using 1.0 ml of anisole and 10 ml of HF at −5° C. for one hour. The HF was evaporated and the peptide resin mixture was washed with ether. The peptide was extracted with 0.5% TFA in water and then with glacial acetic acid. After lyophilization, 57.7 mg of the crude peptide was obtained. The crude peptide (22.6 mg) was purified on a C-18 Vydac preparative column using acetonitrile-water (0.1% TFA) buffer system. 3.5 mg of pure peptide was obtained. Amino acid analysis and FAB-MS confirmed the structure.

Amino Acid Analysis, Ser (2), Ala (2), Sub (1), Nle (2).

EXAMPLES 28–29

The following compounds were synthesized by the methods given above:

(Pic-Ser-Ser)2-Sub-(Gln-NH$_2$)$_2$ |SEQ ID NO: 40|
(Pic-Ser-Phe)2-Sub-(Phe-NH$_2$)$_2$ [SEQ ID NO: 41|

EXAMPLE 30

Formulations for pharmaceutical use incorporating compounds of the present invention can be prepared in various forms and with numerous excipients. Examples of such formulations are given below.

| Tablets/Ingredients | |
|---|---|
| Per Tablet | |
| 1. Active ingredient (Cpd of Form. I) | 0.5 mg |
| 2. Corn Starch | 20 mg |
| 3. Alginic acid | 20 mg |
| 4. Sodium alginate | 20 mg |
| 5. Mg stearate | 1.3 mg |

Procedure for tablets:

| | |
|---|---|
| Step 1 | Blend ingredients No. 1, No. 2, No. 3 and No. 4 in a suitable mixer/blender. |
| Step 2 | Add sufficient water portion-wise to the blend from Step 1 with careful mixing after each addition. Such additions of water and mixing until the mass is of a consistency to permit its conversion to wet granules. |
| Step 3 | The wet mass is converted to granules by passing it through an oscillating granulator using a No. 8 mesh (2.38 mm) screen. |
| Step 4 | The wet granules are then dried in an oven at 140° F. (60° C.) until dry. |
| Step 5 | The dry granules are lubricated with ingredient No. 5 |
| Step 6 | The lubricated granules are compressed on a suitable tablet press. |

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then sterilized by filtration through a 0.22 micron membrane filter and sealed in sterile containers.

SEQUENCE LISTING ( 1 ) GENERAL INFORMATION:

( i i i ) NUMBER OF SEQUENCES: 41

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 3..5
        ( D ) OTHER INFORMATION: /note= "Asp is bound to NH and Lys
            is bound to CO, NH and CO are bound to (CH2)4
            which is bound to mirror image of this peptide."

( i x ) FEATURE:
        ( A ) NAME/KEY: Modified-site
        ( B ) LOCATION: 3..5
        ( D ) OTHER INFORMATION: /note= "Xaa is diaminosuberic
            acid."

( x i ) SEQUENCE DESCRIPTION: SEQ ID NO:1:

Glu  Glu  Asp  Xaa  Lys
    1                       5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 3..5
        ( D ) OTHER INFORMATION: /note= "Asp is bound to NH and Lys
            is bound to CO, NH and CO are bound to (CH2)2
            which is bound to mirror image of this peptide."

( i x ) FEATURE:
        ( A ) NAME/KEY: Modified-site
        ( B ) LOCATION: 3..5
        ( D ) OTHER INFORMATION: /note= "Xaa is diaminoadipic acid."

( x i ) SEQUENCE DESCRIPTION: SEQ ID NO:2:

Glu  Glu  Asp  Xaa  Lys
    1                       5

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 3..5
        ( D ) OTHER INFORMATION: /note= "Glu is bound to NH and Lys
            is bound to CO, NH and CO are bound to (CH2)4

-continued which is bound to mirror image of this peptide."
    ( i x ) FEATURE:
            ( A ) NAME/KEY: Modified-site
            ( B ) LOCATION: 3..5
            ( D ) OTHER INFORMATION: /note= "Xaa is diaminosuberic
                    acid."

( x i ) SEQUENCE DESCRIPTION: SEQ ID NO:3:

Glu  Glu  Glu  Xaa  Lys
    1                   5

( 2 ) INFORMATION FOR SEQ ID NO:4:

( i ) SEQUENCE CHARACTERISTICS:
                ( A ) LENGTH: 5 amino acids
                ( B ) TYPE: amino acid
                ( C ) STRANDEDNESS: unknown
                ( D ) TOPOLOGY: unknown ( i i ) MOLECULE TYPE: peptide ( i x ) FEATURE:
            ( A ) NAME/KEY: Modified-site
            ( B ) LOCATION: 3..5
            ( D ) OTHER INFORMATION: /note= "Asp is bound to NH and Lys
                    is bound to CO, NH and CO are bound to (CH2)4
                    which is bound to mirror image of this peptide."

( i x ) FEATURE:
            ( A ) NAME/KEY: Modified-site
            ( B ) LOCATION: 3..5
            ( D ) OTHER INFORMATION: /note= "Xaa is diaminosuberic
                    acid."

( x i ) SEQUENCE DESCRIPTION: SEQ ID NO:4:

Glu  Asp  Asp  Xaa  Lys
    1                   5

( 2 ) INFORMATION FOR SEQ ID NO:5:

( i ) SEQUENCE CHARACTERISTICS:
                ( A ) LENGTH: 5 amino acids
                ( B ) TYPE: amino acid
                ( C ) STRANDEDNESS: unknown
                ( D ) TOPOLOGY: unknown ( i i ) MOLECULE TYPE: peptide ( i x ) FEATURE:
            ( A ) NAME/KEY: Modified-site
            ( B ) LOCATION: 1..3
            ( D ) OTHER INFORMATION: /note= "Xaa in position 1 is
                    picolinic acid (Pic)."

( i x ) FEATURE:
            ( A ) NAME/KEY: Modified-site
            ( B ) LOCATION: 3..5
            ( D ) OTHER INFORMATION: /note= "Asp is bound to NH and Lys
                    is bound to CO, NH and CO are bound to (CH2)4
                    which is bound to mirror image of this peptide."

( i x ) FEATURE:
            ( A ) NAME/KEY: Modified-site
            ( B ) LOCATION: 3..5
            ( D ) OTHER INFORMATION: /note= "Xaa in position 4 is
                    diaminosuberic acid."

( x i ) SEQUENCE DESCRIPTION: SEQ ID NO:5:

Xaa  Glu  Asp  Xaa  Lys
    1                   5

( 2 ) INFORMATION FOR SEQ ID NO:6:

( i ) SEQUENCE CHARACTERISTICS:
   ( A ) LENGTH: 5 amino acids
   ( B ) TYPE: amino acid
   ( C ) STRANDEDNESS: unknown
   ( D ) TOPOLOGY: unknown ( i i ) MOLECULE TYPE: peptide ( i x ) FEATURE:
   ( A ) NAME/KEY: Modified-site
   ( B ) LOCATION: 1..3
   ( D ) OTHER INFORMATION: /note= "Xaa in position 1 is
     L- pipecolinic acid (L-Ppc)."

( i x ) FEATURE:
   ( A ) NAME/KEY: Modified-site
   ( B ) LOCATION: 3..5
   ( D ) OTHER INFORMATION: /note= "Asp is bound to NH and Lys
     is bound to CO, NH and CO are bound to (CH2)4
     which is bound to mirror image of this peptide."

( i x ) FEATURE:
   ( A ) NAME/KEY: Modified-site
   ( B ) LOCATION: 3..5
   ( D ) OTHER INFORMATION: /note= "Xaa in position 4 is
     diaminosuberic acid."

( x i ) SEQUENCE DESCRIPTION: SEQ ID NO:6:

Xaa Glu Asp Xaa Lys
1       5

( 2 ) INFORMATION FOR SEQ ID NO:7:

( i ) SEQUENCE CHARACTERISTICS:
   ( A ) LENGTH: 5 amino acids
   ( B ) TYPE: amino acid
   ( C ) STRANDEDNESS: unknown
   ( D ) TOPOLOGY: unknown ( i i ) MOLECULE TYPE: peptide ( i x ) FEATURE:
   ( A ) NAME/KEY: Modified-site
   ( B ) LOCATION: 3..5
   ( D ) OTHER INFORMATION: /note= "Asp is bound to NH and Lys
     is bound to CO, NH and CO are bound to (CH2)4
     which is bound to a mirror image of this peptide."

( i x ) FEATURE:
   ( A ) NAME/KEY: Modified-site
   ( B ) LOCATION: 3..5
   ( D ) OTHER INFORMATION: /note= "Xaa is diaminosuberic
     acid."

( x i ) SEQUENCE DESCRIPTION: SEQ ID NO:7:

Glu Ser Asp Xaa Lys
1       5

( 2 ) INFORMATION FOR SEQ ID NO:8:

( i ) SEQUENCE CHARACTERISTICS:
   ( A ) LENGTH: 5 amino acids
   ( B ) TYPE: amino acid
   ( C ) STRANDEDNESS: unknown
   ( D ) TOPOLOGY: unknown ( i i ) MOLECULE TYPE: peptide ( i x ) FEATURE:
   ( A ) NAME/KEY: Modified-site
   ( B ) LOCATION: 3..5
   ( D ) OTHER INFORMATION: /note= "Asp is bound to NH and Lys
     is bound to CO, NH and CO are bound to (CH2)2
     which is bound to mirror image of this peptide."

( i x ) FEATURE:

(A) NAME/KEY: Modified-site
(B) LOCATION: 3..5
(D) OTHER INFORMATION: /note= "Xaa is diaminoadipic acid."

(x i) SEQUENCE DESCRIPTION: SEQ ID NO:8:

```
Glu  Ser  Asp  Xaa  Lys
1                   5
```

(2) INFORMATION FOR SEQ ID NO:9:

(i) SEQUENCE CHARACTERISTICS:
   (A) LENGTH: 5 amino acids
   (B) TYPE: amino acid
   (C) STRANDEDNESS: unknown
   (D) TOPOLOGY: unknown (i i) MOLECULE TYPE: peptide (i x) FEATURE:
   (A) NAME/KEY: Modified-site
   (B) LOCATION: 1..3
   (D) OTHER INFORMATION: /note= "Xaa in position 1 is picolinic acid (Pic)."

(i x) FEATURE:
   (A) NAME/KEY: Modified-site
   (B) LOCATION: 3..5
   (D) OTHER INFORMATION: /note= "Asp is bound to CO, NH and Lys is bound to CO, NH and CO are bound to (CH2)2 which is bound to a mirror image of this peptide."

(i x) FEATURE:
   (A) NAME/KEY: Modified-site
   (B) LOCATION: 3..5
   (D) OTHER INFORMATION: /note= "Xaa in position 4 is diaminoadipic acid."

(x i) SEQUENCE DESCRIPTION: SEQ ID NO:9:

```
Xaa  Ser  Asp  Xaa  Lys
1                   5
```

(2) INFORMATION FOR SEQ ID NO:10:

(i) SEQUENCE CHARACTERISTICS:
   (A) LENGTH: 6 amino acids
   (B) TYPE: amino acid
   (C) STRANDEDNESS: unknown
   (D) TOPOLOGY: unknown (i i) MOLECULE TYPE: peptide (i x) FEATURE:
   (A) NAME/KEY: Modified-site
   (B) LOCATION: 3..5
   (D) OTHER INFORMATION: /note= "Asp is bound to NH and Tyr is bound to CO, NH and CO are bound to (CH2)2 which is bound to a mirror image of this peptide."

(i x) FEATURE:
   (A) NAME/KEY: Modified-site
   (B) LOCATION: 3..5
   (D) OTHER INFORMATION: /note= "Xaa is diaminoadipic acid."

(x i) SEQUENCE DESCRIPTION: SEQ ID NO:10:

```
Glu  Glu  Asp  Xaa  Tyr  Lys
1                   5
```

(2) INFORMATION FOR SEQ ID NO:11:

(i) SEQUENCE CHARACTERISTICS:
   (A) LENGTH: 5 amino acids
   (B) TYPE: amino acid
   (C) STRANDEDNESS: unknown
   (D) TOPOLOGY: unknown ( i i ) MOLECULE TYPE: peptide ( i x ) FEATURE:
    ( A ) NAME/KEY: Modified-site
    ( B ) LOCATION: 1..3
    ( D ) OTHER INFORMATION: /note= "Xaa in position 1 is
        picolinic acid (Pic)."

( i x ) FEATURE:
    ( A ) NAME/KEY: Modified-site
    ( B ) LOCATION: 3..5
    ( D ) OTHER INFORMATION: /note= "Asp is bound to NH and Lys
        is bound to CO, NH and CO are bound to $(CH2)2$
        which is bound to a mirror image of this peptide."

( i x ) FEATURE:
    ( A ) NAME/KEY: Modified-site
    ( B ) LOCATION: 3..5
    ( D ) OTHER INFORMATION: /note= "Xaa in position 4 is
        diaminoadipic acid."

( x i ) SEQUENCE DESCRIPTION: SEQ ID NO:11:

Xaa  Glu  Asp  Xaa  Lys
1                   5

( 2 ) INFORMATION FOR SEQ ID NO:12:

( i ) SEQUENCE CHARACTERISTICS:
    ( A ) LENGTH: 5 amino acids
    ( B ) TYPE: amino acid
    ( C ) STRANDEDNESS: unknown
    ( D ) TOPOLOGY: unknown ( i i ) MOLECULE TYPE: peptide ( i x ) FEATURE:
    ( A ) NAME/KEY: Modified-site
    ( B ) LOCATION: 3..5
    ( D ) OTHER INFORMATION: /note= "Asp is bound to NH and Lys
        is bound to CO, NH and CO are bound to $(CH2)3$
        which is bound to a mirror image of this peptide."

( i x ) FEATURE:
    ( A ) NAME/KEY: Modified-site
    ( B ) LOCATION: 3..5
    ( D ) OTHER INFORMATION: /note= "Xaa is diaminopimelic
        acid."

( x i ) SEQUENCE DESCRIPTION: SEQ ID NO:12:

Glu  Glu  Asp  Xaa  Lys
1                   5

( 2 ) INFORMATION FOR SEQ ID NO:13:

( i ) SEQUENCE CHARACTERISTICS:
    ( A ) LENGTH: 5 amino acids
    ( B ) TYPE: amino acid
    ( C ) STRANDEDNESS: unknown
    ( D ) TOPOLOGY: unknown ( i i ) MOLECULE TYPE: peptide ( i x ) FEATURE:
    ( A ) NAME/KEY: Modified-site
    ( B ) LOCATION: 3..5
    ( D ) OTHER INFORMATION: /note= "Xaa is Lanthionine
        [ SCH2CH(NH2)COOH]which acts as a bridge linking a
        mirror image peptide."

( x i ) SEQUENCE DESCRIPTION: SEQ ID NO:13:

Glu  Glu  Asp  Xaa  Lys
1                   5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 3..5
        ( D ) OTHER INFORMATION: /note= "Asp is bound to NH and Lys
            is bound to CO, NH and CO are bound to (CH2)4
            which is bound to a mirror image of this peptide."

( i x ) FEATURE:
        ( A ) NAME/KEY: Modified-site
        ( B ) LOCATION: 3..5
        ( D ) OTHER INFORMATION: /note= "Xaa is diaminosuberic
            acid."

( x i ) SEQUENCE DESCRIPTION: SEQ ID NO:14:

Pro  Asp  Asp  Xaa  Lys
    1                        5

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 3..5
        ( D ) OTHER INFORMATION: /note= "Asp is bound to NH and Lys
            is bound to CO, NH and CO are bound to (CH2)3
            which is bound to a mirror image of this peptide."

( i x ) FEATURE:
        ( A ) NAME/KEY: Modified-site
        ( B ) LOCATION: 3..5
        ( D ) OTHER INFORMATION: /note= "Xaa is diaminopimelic acid"

( x i ) SEQUENCE DESCRIPTION: SEQ ID NO:15:

Glu  Asp  Asp  Xaa  Lys
    1                        5

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 3..5
        ( D ) OTHER INFORMATION: /note= "Xaa is diaminopimelic
            acid."

( i x ) FEATURE:
        ( A ) NAME/KEY: Modified-site
        ( B ) LOCATION: 3..5
        ( D ) OTHER INFORMATION: /note= "Asp is bound to NH and
            position 5 Xaa is bound to CO, NH & CO are bound
            to (CH2)3 which is bound to mirror image peptide."

( i x ) FEATURE:
   ( A ) NAME/KEY: Modified-site
   ( B ) LOCATION: 3..5
   ( D ) OTHER INFORMATION: /note= "Xaa in position 5 is
         Arg-CONH2"

( x i ) SEQUENCE DESCRIPTION: SEQ ID NO:16:

Glu Glu Asp Xaa Xaa
1               5

( 2 ) INFORMATION FOR SEQ ID NO:17:

( i ) SEQUENCE CHARACTERISTICS:
      ( A ) LENGTH: 5 amino acids
      ( B ) TYPE: amino acid
      ( C ) STRANDEDNESS: unknown
      ( D ) TOPOLOGY: unknown ( i i ) MOLECULE TYPE: peptide ( i x ) FEATURE:
      ( A ) NAME/KEY: Modified-site
      ( B ) LOCATION: 3..5
      ( D ) OTHER INFORMATION: /note= "Asp is bound to NH and Lys
            is bound to CO, NH and CO are bound to (CH2)4
            which is bound to a mirror image of this peptide."

( i x ) FEATURE:
      ( A ) NAME/KEY: Modified-site
      ( B ) LOCATION: 3..5
      ( D ) OTHER INFORMATION: /note= "Xaa is diaminosuberic
            acid."

( x i ) SEQUENCE DESCRIPTION: SEQ ID NO:17:

Thr Glu Asp Xaa Lys
1               5

( 2 ) INFORMATION FOR SEQ ID NO:18:

( i ) SEQUENCE CHARACTERISTICS:
      ( A ) LENGTH: 6 amino acids
      ( B ) TYPE: amino acid
      ( C ) STRANDEDNESS: unknown
      ( D ) TOPOLOGY: unknown ( i i ) MOLECULE TYPE: peptide ( i x ) FEATURE:
      ( A ) NAME/KEY: Modified-site
      ( B ) LOCATION: 4..6
      ( D ) OTHER INFORMATION: /note= "Asp is bound to NH and Lys
            is bound to CO, NH and CO are bound to (CH2)4
            which is bound to a mirror image of this peptide."

( i x ) FEATURE:
      ( A ) NAME/KEY: Modified-site
      ( B ) LOCATION: 4..6
      ( D ) OTHER INFORMATION: /note= "Xaa is diaminosuberic
            acid."

( x i ) SEQUENCE DESCRIPTION: SEQ ID NO:18:

Glu Thr Glu Asp Xaa Lys
1                   5

( 2 ) INFORMATION FOR SEQ ID NO:19:

( i ) SEQUENCE CHARACTERISTICS:
      ( A ) LENGTH: 6 amino acids
      ( B ) TYPE: amino acid
      ( C ) STRANDEDNESS: unknown
      ( D ) TOPOLOGY: unknown ( i i ) MOLECULE TYPE: peptide ( i x ) FEATURE:
  ( A ) NAME/KEY: Modified-site
  ( B ) LOCATION: 4..6
  ( D ) OTHER INFORMATION: /note= "Asp is bound to NH and Lys
       is bound to CO, NH and CO are bound to (CH2)4
       which is bound to a mirror image of this peptide."

( i x ) FEATURE:
  ( A ) NAME/KEY: Modified-site
  ( B ) LOCATION: 4..6
  ( D ) OTHER INFORMATION: /note= "Xaa is diaminosuberic
       acid."

( x i ) SEQUENCE DESCRIPTION: SEQ ID NO:19:

Glu Glu Thr Asp Xaa Lys
1               5

( 2 ) INFORMATION FOR SEQ ID NO:20:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: unknown ( i i ) MOLECULE TYPE: peptide ( i x ) FEATURE:
    ( A ) NAME/KEY: Modified-site
    ( B ) LOCATION: 4..6
    ( D ) OTHER INFORMATION: /note= "Tyr is bound to NH and Lys
         is bound to CO, NH and CO are bound to (CH2)4
         which is bound to a mirror image of this peptide."

( i x ) FEATURE:
    ( A ) NAME/KEY: Modified-site
    ( B ) LOCATION: 4..6
    ( D ) OTHER INFORMATION: /note= "Xaa is diaminosuberic
         acid."

( x i ) SEQUENCE DESCRIPTION: SEQ ID NO:20:

Glu Glu Asp Thr Xaa Lys
1               5

( 2 ) INFORMATION FOR SEQ ID NO:21:

( i ) SEQUENCE CHARACTERISTICS:
    ( A ) LENGTH: 5 amino acids
    ( B ) TYPE: amino acid
    ( C ) STRANDEDNESS: unknown
    ( D ) TOPOLOGY: unknown ( i i ) MOLECULE TYPE: peptide ( i x ) FEATURE:
    ( A ) NAME/KEY: Modified-site
    ( B ) LOCATION: 3..5
    ( D ) OTHER INFORMATION: /note= "Xaa is bis
         BOC-S,S'- 1,3-propanediylcysteine (Prc) which acts
         as a bridge linking a mirror image peptide."

( x i ) SEQUENCE DESCRIPTION: SEQ ID NO:21:

Glu Glu Asp Xaa Lys
1           5

( 2 ) INFORMATION FOR SEQ ID NO:22:

( i ) SEQUENCE CHARACTERISTICS:
    ( A ) LENGTH: 5 amino acids
    ( B ) TYPE: amino acid
    ( C ) STRANDEDNESS: unknown
    ( D ) TOPOLOGY: unknown ( i i ) MOLECULE TYPE: peptide ( i x ) FEATURE:
    ( A ) NAME/KEY: Modified-site
    ( B ) LOCATION: 3..5
    ( D ) OTHER INFORMATION: /note= "Xaa is bis
        BOC-S,S'- 1,2-ethanediylcysteine (Etc) which acts
        as a bridge linking a mirror image peptide."

( x i ) SEQUENCE DESCRIPTION: SEQ ID NO:22:

Glu  Glu  Asp  Xaa  Lys
1                              5

( 2 ) INFORMATION FOR SEQ ID NO:23:

( i ) SEQUENCE CHARACTERISTICS:
    ( A ) LENGTH: 5 amino acids
    ( B ) TYPE: amino acid
    ( C ) STRANDEDNESS: unknown
    ( D ) TOPOLOGY: unknown ( i i ) MOLECULE TYPE: peptide ( i x ) FEATURE:
    ( A ) NAME/KEY: Modified-site
    ( B ) LOCATION: 3..5
    ( D ) OTHER INFORMATION: /note= "Xaa is bis
        BOC-S,S'- 1,4-butanediylcysteine (Buc) which acts
        as a bridge linking a mirror image peptide."

( x i ) SEQUENCE DESCRIPTION: SEQ ID NO:23:

Glu  Glu  Asp  Xaa  Lys
1                              5

( 2 ) INFORMATION FOR SEQ ID NO:24:

( i ) SEQUENCE CHARACTERISTICS:
    ( A ) LENGTH: 5 amino acids
    ( B ) TYPE: amino acid
    ( C ) STRANDEDNESS: unknown
    ( D ) TOPOLOGY: unknown ( i i ) MOLECULE TYPE: peptide ( i x ) FEATURE:
    ( A ) NAME/KEY: Modified-site
    ( B ) LOCATION: 3..5
    ( D ) OTHER INFORMATION: /note= "Asp is bound to NH and
        position 5 Xaa is bound to CO, NH & CO are bound
        to (CH2)4 which is bound to mirror image peptide."

( i x ) FEATURE:
    ( A ) NAME/KEY: Modified-site
    ( B ) LOCATION: 3..5
    ( D ) OTHER INFORMATION: /note= "Xaa in position 4 is
        diaminosuberic acid."

( i x ) FEATURE:
    ( A ) NAME/KEY: Modified-site
    ( B ) LOCATION: 3..5
    ( D ) OTHER INFORMATION: /note= "Xaa in position 5 is
        N- methylarginine (N-MeArg)."

( x i ) SEQUENCE DESCRIPTION: SEQ ID NO:24:

Glu  Glu  Asp  Xaa  Xaa
1                              5

( 2 ) INFORMATION FOR SEQ ID NO:25:

( i ) SEQUENCE CHARACTERISTICS:
    ( A ) LENGTH: 5 amino acids
    ( B ) TYPE: amino acid
    ( C ) STRANDEDNESS: unknown
    ( D ) TOPOLOGY: unknown ( i i ) MOLECULE TYPE: peptide ( i x ) FEATURE:
    ( A ) NAME/KEY: Modified-site
    ( B ) LOCATION: 3..5
    ( D ) OTHER INFORMATION: /note= "Asp is bound to NH and
        position 5 Xaa is bound to CO, NH & CO are bound
        to (CH2)4 which is bound to mirror image peptide."

( i x ) FEATURE:
    ( A ) NAME/KEY: Modified-site
    ( B ) LOCATION: 3..5
    ( D ) OTHER INFORMATION: /note= "Xaa in position 4 is
        diaminosuberic acid."

( i x ) FEATURE:
    ( A ) NAME/KEY: Modified-site
    ( B ) LOCATION: 3..5
    ( D ) OTHER INFORMATION: /note= "Xaa in position 5 is
        diaminohexynoic acid (Hna)."

( x i ) SEQUENCE DESCRIPTION: SEQ ID NO:25:

Glu  Glu  Asp  Xaa  Xaa
1                            5

( 2 ) INFORMATION FOR SEQ ID NO:26:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 1..3
        ( D ) OTHER INFORMATION: /note= "First position Glu is in
            the d- form."

( i x ) FEATURE:
        ( A ) NAME/KEY: Modified-site
        ( B ) LOCATION: 3..5
        ( D ) OTHER INFORMATION: /note= "Asp is bound to NH and Lys
            is bound to CO, NH and CO are bound to (CH2)4
            which is bound to a mirror image of this peptide."

( i x ) FEATURE:
        ( A ) NAME/KEY: Modified-site
        ( B ) LOCATION: 3..5
        ( D ) OTHER INFORMATION: /note= "Xaa is diaminosuberic
            acid."

( x i ) SEQUENCE DESCRIPTION: SEQ ID NO:26:

Glu  Glu  Asp  Xaa  Lys
1                            5

( 2 ) INFORMATION FOR SEQ ID NO:27:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 1..3
        ( D ) OTHER INFORMATION: /note= "Second position Glu is in
            the d- form."

( i x ) FEATURE:
        ( A ) NAME/KEY: Modified-site

-continued ( B ) LOCATION: 3..5
                ( D ) OTHER INFORMATION: /note= "Asp is bound to NH and Lys
                        is bound to CO, NH and CO are bound to (CH2)4
                        which is bound to mirror image of this peptide."

( i x ) FEATURE:
                ( A ) NAME/KEY: Modified-site
                ( B ) LOCATION: 3..5
                ( D ) OTHER INFORMATION: /note= "Xaa is diaminosuberic
                        acid."

( x i ) SEQUENCE DESCRIPTION: SEQ ID NO:27:

Glu  Glu  Asp  Xaa  Lys
    1                   5

( 2 ) INFORMATION FOR SEQ ID NO:28:

( i ) SEQUENCE CHARACTERISTICS:
                ( A ) LENGTH: 5 amino acids
                ( B ) TYPE: amino acid
                ( C ) STRANDEDNESS: unknown
                ( D ) TOPOLOGY: unknown ( i i ) MOLECULE TYPE: peptide ( i x ) FEATURE:
                ( A ) NAME/KEY: Modified-site
                ( B ) LOCATION: 3..5
                ( D ) OTHER INFORMATION: /note= "Lys is bound to NH and Asp
                        is bound to CO, NH and CO are bound to (CH2)4
                        which is bound to mirror image of this peptide."

( i x ) FEATURE:
                ( A ) NAME/KEY: Modified-site
                ( B ) LOCATION: 3..5
                ( D ) OTHER INFORMATION: /note= "Xaa is diaminosuberic
                        acid."

( x i ) SEQUENCE DESCRIPTION: SEQ ID NO:28:

Glu  Glu  Lys  Xaa  Asp
    1                   5

( 2 ) INFORMATION FOR SEQ ID NO:29:

( i ) SEQUENCE CHARACTERISTICS:
                ( A ) LENGTH: 5 amino acids
                ( B ) TYPE: amino acid
                ( C ) STRANDEDNESS: unknown
                ( D ) TOPOLOGY: unknown ( i i ) MOLECULE TYPE: peptide ( i x ) FEATURE:
                ( A ) NAME/KEY: Modified-site
                ( B ) LOCATION: 3..5
                ( D ) OTHER INFORMATION: /note= "Asp is bound to NH and
                        position 5 Xaa is bound to CO, NH & CO are bound
                        to (CH2)2 which is bound to mirror image peptide."

( i x ) FEATURE:
                ( A ) NAME/KEY: Modified-site
                ( B ) LOCATION: 3..5
                ( D ) OTHER INFORMATION: /note= "Xaa in position 4 is
                        diaminoadipic acid."

( i x ) FEATURE:
                ( A ) NAME/KEY: Modified-site
                ( B ) LOCATION: 3..5
                ( D ) OTHER INFORMATION: /note= "Xaa in position 5 is
                        Lys-NH2."

( x i ) SEQUENCE DESCRIPTION: SEQ ID NO:29:

Glu  Ser  Asp  Xaa  Xaa
    1                   5

( 2 ) INFORMATION FOR SEQ ID NO:30:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 1..3
        ( D ) OTHER INFORMATION: /note= "Xaa in position 1 is
            picolinic acid (Pic)."

( i x ) FEATURE:
        ( A ) NAME/KEY: Modified-site
        ( B ) LOCATION: 3..5
        ( D ) OTHER INFORMATION: /note= "Asp is bound to NH and
            position 5 Xaa is bound to CO, NH & CO are bound
            to (CH2)2 which is bound to mirror image peptide."

( i x ) FEATURE:
        ( A ) NAME/KEY: Modified-site
        ( B ) LOCATION: 3..5
        ( D ) OTHER INFORMATION: /note= "Xaa in position 5 is
            Lys-NH2."

( i x ) FEATURE:
        ( A ) NAME/KEY: Modified-site
        ( B ) LOCATION: 3..5
        ( D ) OTHER INFORMATION: /note= "Xaa in position 4 is
            diaminoadipic acid."

( x i ) SEQUENCE DESCRIPTION: SEQ ID NO:30:

Xaa  Ser  Asp  Xaa  Xaa
1                            5

( 2 ) INFORMATION FOR SEQ ID NO:31:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 1..3
        ( D ) OTHER INFORMATION: /note= "Xaa in position 1 is
            picolinic acid (Pic)."

( i x ) FEATURE:
        ( A ) NAME/KEY: Modified-site
        ( B ) LOCATION: 3..5
        ( D ) OTHER INFORMATION: /note= "Asp is bound to NH and
            position 5 Xaa is bound to CO, NH & CO are bound
            to (CH2)2 which is bound to mirror image peptide."

( i x ) FEATURE:
        ( A ) NAME/KEY: Modified-site
        ( B ) LOCATION: 3..5
        ( D ) OTHER INFORMATION: /note= "Xaa in position 5 is
            Lys-NH2."

( i x ) FEATURE:
        ( A ) NAME/KEY: Modified-site
        ( B ) LOCATION: 3..5
        ( D ) OTHER INFORMATION: /note= "Xaa in position 4 is
            diaminoadipic acid."

( x i ) SEQUENCE DESCRIPTION: SEQ ID NO:31:

Xaa  Glu  Asp  Xaa  Xaa (2) INFORMATION FOR SEQ ID NO:32:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 4..6
        (D) OTHER INFORMATION: /note= "Xaa in position four is
            diaminosuberic acid."

(ix) FEATURE:
        (A) NAME/KEY: Modified-site
        (B) LOCATION: 4..6
        (D) OTHER INFORMATION: /note= "Xaa in position 6 is COOH."

(xi) SEQUENCE DESCRIPTION: SEQ ID NO:32:

Glu Glu Asp Xaa Lys Xaa
    1               5

(2) INFORMATION FOR SEQ ID NO:33:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 4..6
        (D) OTHER INFORMATION: /note= "Xaa in position 4 is
            diaminosuberic acid."

(ix) FEATURE:
        (A) NAME/KEY: Modified-site
        (B) LOCATION: 4..6
        (D) OTHER INFORMATION: /note= "Xaa in position 6 is a
            resin."

(xi) SEQUENCE DESCRIPTION: SEQ ID NO:33:

Glu Glu Asp Xaa Lys Xaa
    1               5

(2) INFORMATION FOR SEQ ID NO:34:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 5..7
        (D) OTHER INFORMATION: /note= "Xaa in position 5 is
            diaminosuberic acid."

(ix) FEATURE:
        (A) NAME/KEY: Modified-site
        (B) LOCATION: 5..7
        (D) OTHER INFORMATION: /note= "Xaa in position 7 is a
            resin."

( x i ) SEQUENCE DESCRIPTION: SEQ ID NO:34:

Glu Thr Glu Asp Xaa Lys Xaa
1               5

( 2 ) INFORMATION FOR SEQ ID NO:35:

( i ) SEQUENCE CHARACTERISTICS:
    ( A ) LENGTH: 7 amino acids
    ( B ) TYPE: amino acid
    ( C ) STRANDEDNESS: unknown
    ( D ) TOPOLOGY: unknown ( i i ) MOLECULE TYPE: peptide ( i x ) FEATURE:
    ( A ) NAME/KEY: Modified-site
    ( B ) LOCATION: 5..7
    ( D ) OTHER INFORMATION: /note= "Xaa in position 5 is
           diaminosuberic acid."

( i x ) FEATURE:
    ( A ) NAME/KEY: Modified-site
    ( B ) LOCATION: 5..7
    ( D ) OTHER INFORMATION: /note= "Xaa in position 7 is a
           resin."

( x i ) SEQUENCE DESCRIPTION: SEQ ID NO:35:

Glu Glu Asp Thr Xaa Lys Xaa
1               5

( 2 ) INFORMATION FOR SEQ ID NO:36:

( i ) SEQUENCE CHARACTERISTICS:
    ( A ) LENGTH: 7 amino acids
    ( B ) TYPE: amino acid
    ( C ) STRANDEDNESS: unknown
    ( D ) TOPOLOGY: unknown ( i i ) MOLECULE TYPE: peptide ( i x ) FEATURE:
    ( A ) NAME/KEY: Modified-site
    ( B ) LOCATION: 5..7
    ( D ) OTHER INFORMATION: /note= "Xaa in position 5 is
           diaminosuberic acid."

( i x ) FEATURE:
    ( A ) NAME/KEY: Modified-site
    ( B ) LOCATION: 5..7
    ( D ) OTHER INFORMATION: /note= "Xaa in position 7 is a
           resin."

( x i ) SEQUENCE DESCRIPTION: SEQ ID NO:36:

Glu Glu Thr Asp Xaa Lys Xaa
1               5

( 2 ) INFORMATION FOR SEQ ID NO:37:

( i ) SEQUENCE CHARACTERISTICS:
    ( A ) LENGTH: 5 amino acids
    ( B ) TYPE: amino acid
    ( C ) STRANDEDNESS: unknown
    ( D ) TOPOLOGY: unknown ( i i ) MOLECULE TYPE: peptide ( i x ) FEATURE:
    ( A ) NAME/KEY: Modified-site
    ( B ) LOCATION: 1..3
    ( D ) OTHER INFORMATION: /note= "Xaa in position 1 is
           picolinic acid (Pic)."

( i x ) FEATURE:
    ( A ) NAME/KEY: Modified-site ( B ) LOCATION: 3..5
( D ) OTHER INFORMATION: /note= "Asp is bound to NH and
position 5 Xaa is bound to CO, NH & CO are bound
to (CH2)2 which is bound to mirror image peptide."

( i x ) FEATURE:
( A ) NAME/KEY: Modified-site
( B ) LOCATION: 3..5
( D ) OTHER INFORMATION: /note= "Xaa in position 4 is
diaminoadipic acid."

( i x ) FEATURE:
( A ) NAME/KEY: Modified-site
( B ) LOCATION: 3..5
( D ) OTHER INFORMATION: /note= "Xaa in position 5 ix
Lys- CONH2."

( x i ) SEQUENCE DESCRIPTION: SEQ ID NO:37:

Xaa  Ser  Asp  Xaa  Xaa
1                    5

( 2 ) INFORMATION FOR SEQ ID NO:38:

( i ) SEQUENCE CHARACTERISTICS:
( A ) LENGTH: 5 amino acids
( B ) TYPE: amino acid
( C ) STRANDEDNESS: unknown
( D ) TOPOLOGY: unknown ( i i ) MOLECULE TYPE: peptide ( i x ) FEATURE:
( A ) NAME/KEY: Modified-site
( B ) LOCATION: 3..5
( D ) OTHER INFORMATION: /note= "Asp is bound to NH and
position 5 Xaa is bound to CO, NH & CO are bound
to (CH2)4 which is bound to mirror image peptide."

( i x ) FEATURE:
( A ) NAME/KEY: Modified-site
( B ) LOCATION: 3..5
( D ) OTHER INFORMATION: /note= "Xaa in position 4 is
diaminosuberic acid."

( i x ) FEATURE:
( A ) NAME/KEY: Modified-site
( B ) LOCATION: 3..5
( D ) OTHER INFORMATION: /note= "Xaa in position 5 is
Lys-NH2."

( x i ) SEQUENCE DESCRIPTION: SEQ ID NO:38:

Glu  Glu  Asp  Xaa  Xaa
1                    5

( 2 ) INFORMATION FOR SEQ ID NO:39:

( i ) SEQUENCE CHARACTERISTICS:
( A ) LENGTH: 5 amino acids
( B ) TYPE: amino acid
( C ) STRANDEDNESS: unknown
( D ) TOPOLOGY: unknown ( i i ) MOLECULE TYPE: peptide ( i x ) FEATURE:
( A ) NAME/KEY: Modified-site
( B ) LOCATION: 3..5
( D ) OTHER INFORMATION: /note= "Ala is bound to NH and
position 5 Xaa is bound to CO, NH & CO are bound
to (CH2)4 which is bound to mirror image peptide."

( i x ) FEATURE:
( A ) NAME/KEY: Modified-site
( B ) LOCATION: 3..5
( D ) OTHER INFORMATION: /note= "Xaa in position 1 is
picolinic acid (Pic)."

( i x ) FEATURE:
   ( A ) NAME/KEY: Modified-site
   ( B ) LOCATION: 3..5
   ( D ) OTHER INFORMATION: /note= "Xaa in position 4 is
         diaminosuberic acid."

( i x ) FEATURE:
   ( A ) NAME/KEY: Modified-site
   ( B ) LOCATION: 3..5
   ( D ) OTHER INFORMATION: /note= "Xaa in position 5 is
         Nle-NH2."

( x i ) SEQUENCE DESCRIPTION: SEQ ID NO:39:

Xaa  Ser  Ala  Xaa  Xaa
1                    5

( 2 ) INFORMATION FOR SEQ ID NO:40:

( i ) SEQUENCE CHARACTERISTICS:
      ( A ) LENGTH: 5 amino acids
      ( B ) TYPE: amino acid
      ( C ) STRANDEDNESS: unknown
      ( D ) TOPOLOGY: unknown ( i i ) MOLECULE TYPE: peptide ( i x ) FEATURE:
      ( A ) NAME/KEY: Modified-site
      ( B ) LOCATION: 3..5
      ( D ) OTHER INFORMATION: /note= "Ser is bound to NH and
            position 5 Xaa is bound to CO, NH & CO are bound
            to (CH2)4 which is bound to mirror image peptide."

( i x ) FEATURE:
      ( A ) NAME/KEY: Modified-site
      ( B ) LOCATION: 3..5
      ( D ) OTHER INFORMATION: /note= "Xaa in position 1 is
            picolinic acid (Pic)."

( i x ) FEATURE:
      ( A ) NAME/KEY: Modified-site
      ( B ) LOCATION: 3..5
      ( D ) OTHER INFORMATION: /note= "Xaa in position 4 is
            diaminosuberic acid."

( i x ) FEATURE:
      ( A ) NAME/KEY: Modified-site
      ( B ) LOCATION: 3..5
      ( D ) OTHER INFORMATION: /note= "Xaa in position 5 is
            Gln-NH2."

( x i ) SEQUENCE DESCRIPTION: SEQ ID NO:40:

Xaa  Ser  Ser  Xaa  Xaa
1                    5

( 2 ) INFORMATION FOR SEQ ID NO:41:

( i ) SEQUENCE CHARACTERISTICS:
      ( A ) LENGTH: 5 amino acids
      ( B ) TYPE: amino acid
      ( C ) STRANDEDNESS: unknown
      ( D ) TOPOLOGY: unknown ( i i ) MOLECULE TYPE: peptide ( i x ) FEATURE:
      ( A ) NAME/KEY: Modified-site
      ( B ) LOCATION: 3..5
      ( D ) OTHER INFORMATION: /note= "Phe is bound to NH and
            position 5 Xaa is bound to CO, NH & CO are bound
            to (CH2)4 which is bound to mirror image peptide."

( i x ) FEATURE:
      ( A ) NAME/KEY: Modified-site
      ( B ) LOCATION: 3..5

```
( D ) OTHER INFORMATION: /note= "Xaa in position 1 is
    picolinic acid (Pic)."

( i x ) FEATURE:
    ( A ) NAME/KEY: Modified-site
    ( B ) LOCATION: 3..5
    ( D ) OTHER INFORMATION: /note= "Xaa in position 4 is
        diaminosuberic acid."

( i x ) FEATURE:
    ( A ) NAME/KEY: Modified-site
    ( B ) LOCATION: 3..5
    ( D ) OTHER INFORMATION: /note= "Xaa in position 5 is
        Phe-NH2."

( x i ) SEQUENCE DESCRIPTION: SEQ ID NO:41:

Xaa  Ser  Phe  Xaa  Xaa
1                   5
```

We claim:

1. A method of preventing viral, fungal and bacterial infections which comprises administering to a subject in need thereof, an effective amount of a compound of Formula (I):

$$\begin{array}{c} A-B-C-E-NH \diagdown \quad \diagup CO-F-D \\ CH \\ | \\ (CH_2)_m \\ | \\ CH \\ \diagup \quad \diagdown \\ A-B-C-E-NH \quad CO-F-D \end{array} \quad (I)$$

wherein:

m is 1, 2 or 4;

A is pyroglutamic acid, proline, glutamine, glutamic acid, picolinic acid, pipecolinic acid, pyrrole carboxylic acid, isopyrrole carboxylic acid, pyrazole carboxylic acid, isoimidazole carboxylic acid, triazole carboxylic acid, pyrimidine carboxylic acid, pyridine carboxylic acid, pyridazine carboxylic acid, pyrazine carboxylic acid, piperazine carboxylic acid, triazine carboxylic acid or morpholine carboxylic acid;

B is serine, theronine, glutamic acid, or aspartic acid;

C is glutamic acid or aspartic acid;

D is lysine or the carboxyamide derivative thereof;

E is glutamic acid, aspartic acid or a peptide bond;

F is tyrosine or a peptide bond;

or a pharmaceutically acceptable salt thereof.

2. A method of preventing viral, fungal and bacterial infections which comprises administering to a subject in need thereof, an effective amount of a compound of claim 1 which is (pglu-Glu-Asp)$_2$-Sub-(Lys)$_2$ [SEQ ID NO: 1].

3. A method of preventing viral, fungal and bacterial infections which comprises administering to a subject in need thereof, an effective amount of a compound of claim 1 chosen from the group consisting of:

(pGlu-Glu-Asp)$_2$Adp(Lys)$_2$ [SEQ ID NO: 2]

(pGlu-Glu-Glu)$_2$Sub(Lys)$_2$ [SEQ ID NO: 3]

(pGlu-Asp-Asp)$_2$Sub(Lys)$_2$ [SEQ ID NO: 4]

(Pic-Glu-Asp)$_2$Sub(Lys)$_2$ [SEQ ID NO: 5]

(L-Ppc-Glu-Asp)$_2$Sub(Lys)$_2$ [SEQ ID NO: 6]

(pGlu-Ser-Asp)$_2$Sub(Lys)$_2$ [SEQ ID NO: 7]

(pGlu-Ser-Asp)$_2$Adp(Lys)$_2$ [SEQ ID NO: 8]

(pGlu-Ser-Asp)$_2$Adp(Lys-NH$_2$)$_2$ [SEQ ID NO: 29]

(Pic-Ser-Asp)$_2$Adp(Lys)$_2$ [SEQ ID NO: 9]

(Pic-Ser-Asp)$_2$Adp(Lys-NH$_2$)$_2$[SEQ ID NO: 30] or (pGlu-Glu-Asp)$_2$-Adp(Tyr-Lys)$_2$ [SEQ ID NO: 10].

4. A method of preventing Candida or Herpes infection which comprises administering to a subject in need thereof, an effective amount of a compound of claim 1.

5. A method of preventing Candida or Herpes infection which comprises administering to a subject in need thereof, an effective amount of a compound of claim 1 which is (pglu-Glu-Asp)$_2$-Sub-(Lys$_2$ [SEQ ID NO: 1].

6. A method of treating viral, fungal and bacterial infections which comprises administering to a subject in need thereof, an effective amount of a compound of Formula (I):

$$\begin{array}{c} A-B-C-E-NH \diagdown \quad \diagup CO-F-D \\ CH \\ | \\ (CH_2)_m \\ | \\ CH \\ \diagup \quad \diagdown \\ A-B-C-E-NH \quad CO-F-D \end{array} \quad (I)$$

wherein:

m is 1, 2 or 4;

A is pyroglutamic acid, proline, glutamine, glutamic acid, picolinic acid, pipecolinic acid, pyrrole carboxylic acid, isopyrrole carboxylic acid, pyrazole carboxylic acid, isoimidazole carboxylic acid, triazole carboxylic acid, pyrimidine carboxylic acid, pyridine carboxylic acid, pyridazine carboxylic acid, pyrazine carboxylic acid, piperazine carboxylic acid, triazine carboxylic acid or morpholine carboxylic acid;

B is serine, theronine, glutamic acid, or aspartic acid;

C is glutamic acid or aspartic acid;

D is lysine or the carboxyamide derivative thereof;

E is glutamic acid, aspartic acid or a peptide bond;

F is tyrosine or a peptide bond;

or a pharmaceutically acceptable salt thereof.

7. A method of treating viral, fungal and bacterial infections which comprises administering to a subject in need thereof, an effective amount of a compound of claim 6 which is (pglu-Glu-Asp)$_2$-Sub-(Lys)$_2$ [SEQ ID NO: 1].

8. A method of treating viral, fungal and bacterial infections which comprises administering to a subject in need thereof, an effective amount of a compound of claim 6 chosen from the group consisting of:

(pGlu-Glu-Asp)$_2$Adp(Lys)$_2$ [SEQ ID NO: 2]

(pGlu-Glu-Glu)₂Sub(Lys)₂ [SEQ ID NO: 3]
(pGlu-Asp-Asp)₂Sub(Lys)₂ [SEQ ID NO: 4]
(Pic-Glu-Asp)₂Sub(Lys)₂ [SEQ ID NO: 5]
(L-Ppc-Glu-Asp)₂Sub(Lys)₂ [SEQ ID NO: 6]
(pGlu-Ser-Asp)₂Sub(Lys)₂ [SEQ ID NO: 7]
(pGlu-Ser-Asp)₂Adp(Lys)₂ [SEQ ID NO: 8]
(pGlu-Ser-Asp)₂Adp(Lys-NH₂)₂ [SEQ ID NO: 29]
(Pic-Ser-Asp)₂Adp(Lys)₂ [SEQ ID NO: 9]
(Pic-Ser-Asp)₂Adp(Lys-NH₂)₂ [SEQ ID NO: 30] or
(pGlu-Glu-Asp)₂-Adp(Tyr-Lys)₂ [SEQ ID NO: 10].

9. A method of treating Candida or Herpes infection which comprises administering to a subject in need thereof, an effective amount of a compound of claim 6.

10. A method of treating Candida or Herpes infection which comprises administering to a subject in need thereof, an effective amount of a compound of claim 6 which is (pglu-Glu-Asp)₂-Sub-(Lys)₂ [SEQ ID NO: 1].

* * * * *